United States Patent
Liao

(10) Patent No.: US 11,103,707 B2
(45) Date of Patent: *Aug. 31, 2021

(54) METHODS AND SYSTEMS TO DIAGNOSE DEPRESSION

(71) Applicant: LivaNova USA, Inc., Houston, TX (US)

(72) Inventor: Wangcai Liao, Houston, TX (US)

(73) Assignee: LivaNova USA, Inc., Houston, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/288,238

(22) Filed: Feb. 28, 2019

(65) Prior Publication Data

US 2019/0192856 A1 Jun. 27, 2019

Related U.S. Application Data

(63) Continuation of application No. 13/746,478, filed on Jan. 22, 2013, now Pat. No. 10,220,211.

(51) Int. Cl.
*A61N 1/36* (2006.01)
*A61B 5/00* (2006.01)
(Continued)

(52) U.S. Cl.
CPC .......... *A61N 1/36096* (2013.01); *A61B 5/165* (2013.01); *A61B 5/4836* (2013.01);
(Continued)

(58) Field of Classification Search
None
See application file for complete search history.

(56) References Cited

U.S. PATENT DOCUMENTS 4,172,459 A 10/1979 Hepp
4,197,856 A 4/1980 Northrop
(Continued)

FOREIGN PATENT DOCUMENTS

EP 1 145 736 A2 10/2001
EP 1 486 232 12/2004
(Continued)

OTHER PUBLICATIONS

Baevskii, R.M. "Analysis of Heart Rate Variability in Space Medicine," Human Physiology, vol. 28, No. 2, (2002); pp. 202-213.
(Continued)

*Primary Examiner* — Joseph M Dietrich
(74) *Attorney, Agent, or Firm* — Foley & Lardner LLP

(57) ABSTRACT

A method includes receiving sensor data at a processor from sensors of an external medical device. The sensor data corresponds to at least a first body parameter value for a patient and a second body parameter value for the patient. The method includes determining a first depression-indicative value based on the first body parameter value, a second depression-indicative value based on the second body parameter value, a depression detection value as a function of a first weight applied to the first depression-indicative value and a second weight applied to the second depression-indicative value, and a depression state based at least in part on a comparison of the depression detection value to one or more threshold values.

20 Claims, 4 Drawing Sheets

(51) Int. Cl.
*A61N 1/05* (2006.01)
*A61B 5/16* (2006.01)
*G16H 50/20* (2018.01)
*G16H 20/70* (2018.01)
*A61B 5/01* (2006.01)
*A61B 5/0205* (2006.01)
*A61B 5/24* (2021.01)

(52) U.S. Cl.
CPC ........... *A61N 1/0529* (2013.01); *G16H 20/70* (2018.01); *G16H 50/20* (2018.01); *A61B 5/01* (2013.01); *A61B 5/0205* (2013.01); *A61B 5/24* (2021.01)

(56) References Cited

U.S. PATENT DOCUMENTS

| | | |
|---|---|---|
| 4,291,699 A | 9/1981 | Geddes et al. |
| 4,320,766 A | 3/1982 | Alihanka et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,062,169 A | 11/1991 | Kennedy et al. |
| 5,113,869 A | 5/1992 | Nappholz et al. |
| 5,137,020 A | 8/1992 | Wayne et al. |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,194,847 A | 3/1993 | Taylor et al. |
| 5,203,326 A | 4/1993 | Collins |
| 5,205,285 A | 4/1993 | Baker, Jr. |
| 5,213,568 A | 5/1993 | Lattin et al. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,513,649 A | 5/1996 | Gevins et al. |
| 5,522,862 A | 6/1996 | Testerman et al. |
| 5,523,742 A | 6/1996 | Simkins et al. |
| 5,540,730 A | 7/1996 | Terry, Jr. et al. |
| 5,540,734 A | 7/1996 | Zabara |
| 5,571,150 A | 11/1996 | Wernicke et al. |
| 5,610,590 A | 3/1997 | Johnson et al. |
| 5,611,350 A | 3/1997 | John |
| 5,645,077 A | 7/1997 | Foxlin |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,748,113 A | 5/1998 | Torch |
| 5,749,900 A | 5/1998 | Schroeppel et al. |
| 5,800,474 A | 9/1998 | Benabid et al. |
| 5,807,284 A | 9/1998 | Foxlin |
| 5,808,552 A | 9/1998 | Wiley et al. |
| 5,792,186 A | 11/1998 | Rise |
| 5,833,709 A | 11/1998 | Rise et al. |
| 5,853,005 A | 12/1998 | Scanlon |
| 5,879,309 A | 3/1999 | Johnson et al. |
| 5,882,203 A | 3/1999 | Correa et al. |
| 5,905,436 A | 5/1999 | Dwight et al. |
| 5,913,876 A | 6/1999 | Taylor et al. |
| 5,916,181 A | 6/1999 | Socci et al. |
| 5,916,239 A | 6/1999 | Geddes et al. |
| 5,928,272 A | 7/1999 | Adkins et al. |
| 5,941,906 A | 8/1999 | Barreras et al. |
| 5,942,979 A | 8/1999 | Luppino |
| 5,978,702 A | 11/1999 | Ward et al. |
| 5,978,972 A | 11/1999 | Stewart et al. |
| 5,987,352 A | 11/1999 | Klein et al. |
| 5,995,868 A | 11/1999 | Dorfmeister et al. |
| 6,016,449 A | 1/2000 | Fischell et al. |
| 6,018,682 A | 1/2000 | Rise |
| 6,048,324 A | 4/2000 | Socci et al. |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,095,991 A | 8/2000 | Krausman et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,162,191 A | 12/2000 | Foxlin |
| 6,163,281 A | 12/2000 | Torch |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,246,344 B1 | 6/2001 | Torch |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,315,740 B1 | 11/2001 | Singh |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,361,507 B1 | 3/2002 | Foxlin |
| 6,361,508 B1 | 3/2002 | Johnson et al. |
| 6,366,813 B1 | 4/2002 | DiLorenzo |
| 6,366,814 B1 | 4/2002 | Boveja et al. |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,441,731 B1 | 8/2002 | Hess |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |

(56) References Cited

U.S. PATENT DOCUMENTS

| | | |
|---|---|---|
| 6,505,074 B2 | 1/2003 | Boveja et al. |
| 6,532,388 B1 | 3/2003 | Hill et al. |
| 6,539,263 B1 | 3/2003 | Schiff et al. |
| 6,542,081 B2 | 4/2003 | Torch |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,611,783 B2 | 8/2003 | Kelly et al. |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,629,990 B2 | 10/2003 | Putz et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Bogeja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,730,047 B2 | 5/2004 | Socci et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,763,256 B2 | 7/2004 | Kimball et al. |
| 6,768,969 B1 | 7/2004 | Nikitin et al. |
| 6,786,877 B2 | 9/2004 | Foxlin |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,850,601 B2 | 2/2005 | Jones et al. |
| 6,879,850 B2 | 4/2005 | Kimball |
| 6,885,888 B2 | 4/2005 | Rezai |
| 6,904,390 B2 | 6/2005 | Nikitin et al. |
| 6,920,357 B2 | 7/2005 | Osorio et al. |
| 6,923,784 B2 | 8/2005 | Stein |
| 6,931,274 B2 | 8/2005 | Williams |
| 6,934,580 B1 | 8/2005 | Osorio et al. |
| 6,934,585 B1 | 8/2005 | Schloss et al. |
| 6,944,501 B1 | 9/2005 | Pless |
| 6,957,107 B2 | 10/2005 | Rogers et al. |
| 6,961,618 B2 | 11/2005 | Osorio et al. |
| 6,984,993 B2 | 1/2006 | Ariav |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,035,684 B2 | 4/2006 | Lee |
| 7,054,792 B2 | 5/2006 | Frei et al. |
| 7,058,453 B2 | 6/2006 | Nelson et al. |
| 7,068,842 B2 | 6/2006 | Liang et al. |
| 7,076,288 B2 | 7/2006 | Skinner |
| 7,077,810 B2 | 7/2006 | Lange et al. |
| 7,079,977 B2 | 7/2006 | Osorio et al. |
| 7,104,947 B2 | 9/2006 | Riehl |
| 7,110,820 B2 | 9/2006 | Tcheng et al. |
| 7,112,319 B2 | 9/2006 | Broderick et al. |
| 7,127,370 B2 | 10/2006 | Kelly et al. |
| 7,134,996 B2 | 11/2006 | Bardy |
| 7,139,677 B2 | 11/2006 | Hively |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| RE39,539 E | 4/2007 | Torch |
| 7,204,833 B1 | 4/2007 | Osorio et al. |
| 7,209,786 B2 | 4/2007 | Brockway et al. |
| 7,209,787 B2 | 4/2007 | DiLorenzo |
| 7,221,981 B2 | 5/2007 | Gliner |
| 7,228,167 B2 | 6/2007 | Kara et al. |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,274,298 B2 | 9/2007 | Frank |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,304,580 B2 | 12/2007 | Sullivan et al. |
| 7,305,268 B2 | 12/2007 | Gliner et al. |
| 7,313,440 B2 | 12/2007 | Miesel |
| 7,314,451 B2 | 1/2008 | Halperin et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,330,760 B2 | 2/2008 | Heruth et al. |
| 7,346,391 B2 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,385,443 B1 | 6/2008 | Denison |
| 7,389,144 B1 | 6/2008 | Osorio et al. |
| 7,389,147 B2 | 6/2008 | Wahlstrand et al. |
| 7,395,113 B2 | 7/2008 | Heruth et al. |
| 7,401,008 B2 | 7/2008 | Frei et al. |
| 7,403,820 B2 | 7/2008 | DiLorenzo |
| 7,420,472 B2 | 9/2008 | Tran |
| 7,433,732 B1 | 10/2008 | Carney et al. |
| 7,447,545 B2 | 11/2008 | Heruth et al. |
| 7,454,245 B2 | 11/2008 | Armstrong et al. |
| 7,488,293 B2 | 2/2009 | Marcovecchio et al. |
| 7,488,294 B2 | 2/2009 | Torch |
| 7,491,181 B2 | 2/2009 | Heruth et al. |
| 7,494,464 B2 | 2/2009 | Rzesnitzek et al. |
| 7,502,643 B2 | 3/2009 | Farringdon et al. |
| 7,515,054 B2 | 4/2009 | Torch |
| 7,539,532 B2 | 5/2009 | Tran |
| 7,539,533 B2 | 5/2009 | Tran |
| 7,539,543 B2 | 5/2009 | Schiff et al. |
| 7,558,622 B2 | 7/2009 | Tran |
| 7,565,132 B2 | 7/2009 | Ben Ayed |
| 7,590,453 B2 | 9/2009 | Heruth et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,658,112 B2 | 2/2010 | Nakamura |
| 7,666,151 B2 | 2/2010 | Sullivan et al. |
| 7,714,757 B2 | 5/2010 | Denison et al. |
| 7,717,848 B2 | 5/2010 | Heruth et al. |
| RE41,376 E | 6/2010 | Torch |
| 7,733,224 B2 | 6/2010 | Tran |

(56) References Cited

U.S. PATENT DOCUMENTS

| | | |
|---|---|---|
| 7,747,318 B2 | 6/2010 | John et al. |
| 7,769,464 B2 | 8/2010 | Gerber et al. |
| 7,775,993 B2 | 8/2010 | Heruth et al. |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,813,802 B2 | 10/2010 | Tcheng et al. |
| 7,822,481 B2 | 10/2010 | Gerber et al. |
| 7,827,011 B2 | 11/2010 | Devaul et al. |
| 7,831,305 B2 | 11/2010 | Gliner |
| 7,847,628 B2 | 12/2010 | Denison |
| 7,866,212 B2 | 1/2011 | Ariav et al. |
| 7,899,545 B2 | 3/2011 | John |
| 7,935,076 B2 | 5/2011 | Estes et al. |
| RE42,471 E | 6/2011 | Torch |
| 7,957,809 B2 | 6/2011 | Bourget et al. |
| 7,965,833 B2 | 6/2011 | Meir et al. |
| 7,974,671 B2 | 7/2011 | Fujiwara et al. |
| 7,979,130 B2 | 7/2011 | Carlson et al. |
| 7,996,076 B2 | 8/2011 | Burns et al. |
| 7,999,857 B2 | 8/2011 | Bunn et al. |
| 8,000,789 B2 | 8/2011 | Denison |
| 8,000,794 B2 | 8/2011 | Lozano |
| 8,021,299 B2 | 9/2011 | Miesel et al. |
| 8,027,730 B2 | 9/2011 | John |
| 8,027,737 B2 | 9/2011 | Kokones et al. |
| 8,075,499 B2 | 12/2011 | Nathan et al. |
| 8,109,891 B2 | 2/2012 | Kramer et al. |
| 8,135,473 B2 | 3/2012 | Miesel et al. |
| 8,337,404 B2 | 12/2012 | Osorio |
| 8,382,667 B2 | 2/2013 | Osorio |
| 8,852,100 B2 | 10/2014 | Osorio |
| 8,951,192 B2 | 2/2015 | Osorio |
| 10,220,211 B2 * | 3/2019 | Liao .................. A61N 1/0529 |
| 2001/0032059 A1 | 10/2001 | Kelly et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0128563 A1 | 9/2002 | Carlson et al. |
| 2002/0151939 A1 | 10/2002 | Rezai |
| 2002/0188214 A1 | 12/2002 | Misczynski et al. |
| 2003/0040680 A1 | 2/2003 | Hassert et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak, III |
| 2003/0195588 A1 | 10/2003 | Fischell et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236474 A1 | 12/2003 | Singh |
| 2003/0236558 A1 | 12/2003 | Whitehurst et al. |
| 2004/0006278 A1 | 1/2004 | Webb et al. |
| 2004/0030365 A1 | 2/2004 | Rubin |
| 2004/0088024 A1 | 5/2004 | Firlik et al. |
| 2004/0111045 A1 | 6/2004 | Sullivan et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0225335 A1 | 11/2004 | Whitehurst et al. |
| 2004/0249302 A1 | 12/2004 | Donoghue et al. |
| 2004/0249416 A1 | 12/2004 | Yun et al. |
| 2004/0267152 A1 | 12/2004 | Pineda |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0022606 A1 | 2/2005 | Partin et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060001 A1 | 3/2005 | Singhal et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0107716 A1 | 5/2005 | Eaton et al. |
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0203366 A1 | 9/2005 | Donoghue et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja et al. |
| 2006/0018833 A1 | 1/2006 | Murphy et al. |
| 2006/0074450 A1 | 4/2006 | Boveja et al. |
| 2006/0079936 A1 | 4/2006 | Boveja et al. |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0149139 A1 | 7/2006 | Bonmassar et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | Kenknight et al. |
| 2006/0200206 A1 | 9/2006 | Firlik et al. |
| 2006/0212091 A1 | 9/2006 | Lozano et al. |
| 2006/0212097 A1 | 9/2006 | Varadan et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |

(56) References Cited

U.S. PATENT DOCUMENTS

| | | |
|---|---|---|
| 2006/0241725 A1 | 10/2006 | Libbus et al. |
| 2006/0293720 A1 | 12/2006 | DiLorenzo |
| 2007/0027486 A1 | 2/2007 | Armstrong |
| 2007/0027497 A1 | 2/2007 | Parnis |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0118054 A1 | 5/2007 | Pinhas et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0242661 A1 | 10/2007 | Tran |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0004904 A1 | 1/2008 | Tran et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081958 A1 | 4/2008 | Denison et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | Leboeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0208013 A1 | 8/2008 | Zhang et al. |
| 2008/0208284 A1 | 8/2008 | Rezai et al. |
| 2008/0258907 A1 | 10/2008 | Kalpaxis |
| 2008/0269579 A1 | 10/2008 | Schiebler |
| 2008/0275327 A1 | 11/2008 | Faarbaek et al. |
| 2008/0275328 A1 | 11/2008 | Jones |
| 2008/0275349 A1 | 11/2008 | Halperin et al. |
| 2008/0281376 A1 | 11/2008 | Gerber et al. |
| 2008/0281381 A1 | 11/2008 | Gerber et al. |
| 2008/0281550 A1 | 11/2008 | Hogle et al. |
| 2008/0319281 A1 | 12/2008 | Aarts |
| 2009/0030345 A1 | 1/2009 | Bonnet et al. |
| 2009/0040052 A1 | 2/2009 | Cameron et al. |
| 2009/0054737 A1 | 2/2009 | Magar et al. |
| 2009/0054742 A1 | 2/2009 | Kaminska et al. |
| 2009/0060287 A1 | 3/2009 | Hyde et al. |
| 2009/0076350 A1 | 3/2009 | Bly et al. |
| 2009/0099624 A1 | 4/2009 | Kokones et al. |
| 2009/0099627 A1 | 4/2009 | Molnar et al. |
| 2009/0105785 A1 | 4/2009 | Wei et al. |
| 2009/0125076 A1 | 5/2009 | Shuros et al. |
| 2009/0137921 A1 | 5/2009 | Kramer et al. |
| 2009/0227882 A1 | 9/2009 | Foo |
| 2009/0227888 A1 | 9/2009 | Salmi et al. |
| 2009/0322540 A1 | 12/2009 | Richardson et al. |
| 2009/0326616 A1 | 12/2009 | Aarts et al. |
| 2010/0010382 A1 | 1/2010 | Panken |
| 2010/0010392 A1 | 1/2010 | Skelton et al. |
| 2010/0010583 A1 | 1/2010 | Panken et al. |
| 2010/0023348 A1 | 1/2010 | Hardee et al. |
| 2010/0056878 A1 | 3/2010 | Partin et al. |
| 2010/0106217 A1 | 4/2010 | Colborn |
| 2010/0109875 A1 | 5/2010 | Ayon et al. |
| 2010/0121214 A1 | 5/2010 | Giftakis et al. |
| 2010/0217533 A1 | 8/2010 | Nadkarni et al. |
| 2010/0223020 A1 | 9/2010 | Goetz |
| 2010/0228103 A1 | 9/2010 | Schecter |
| 2010/0228314 A1 | 9/2010 | Goetz |
| 2010/0268056 A1 | 10/2010 | Picard et al. |
| 2010/0280336 A1 | 11/2010 | Giftakis et al. |
| 2010/0280578 A1 | 11/2010 | Skelton et al. |
| 2010/0280579 A1 | 11/2010 | Denison et al. |
| 2010/0286567 A1 | 11/2010 | Wolfe et al. |
| 2010/0298661 A1 | 11/2010 | McCombie et al. |
| 2010/0298742 A1 | 11/2010 | Perlman et al. |
| 2010/0305665 A1 | 12/2010 | Miesel et al. |
| 2010/0312188 A1 | 12/2010 | Robertson et al. |
| 2011/0029044 A1 | 2/2011 | Hyde et al. |
| 2011/0040204 A1 | 2/2011 | Ivorra et al. |
| 2011/0040546 A1 | 2/2011 | Gerber et al. |
| 2011/0060252 A1 | 3/2011 | Simonsen et al. |
| 2011/0066062 A1 | 3/2011 | Banet et al. |
| 2011/0066081 A1 | 3/2011 | Goto |
| 2011/0112603 A1 | 5/2011 | Degiorgio et al. |
| 2011/0137372 A1 | 6/2011 | Makous et al. |
| 2011/0172545 A1 | 7/2011 | Grudic et al. |
| 2011/0230730 A1 | 9/2011 | Quigg et al. |
| 2011/0245629 A1 | 10/2011 | Giftakis et al. |
| 2011/0251468 A1 | 10/2011 | Osorio |
| 2011/0251469 A1 | 10/2011 | Varadan |
| 2011/0270117 A1 | 11/2011 | Warwick et al. |
| 2011/0270134 A1 | 11/2011 | Skelton |
| 2011/0270346 A1 | 11/2011 | Frei et al. |
| 2011/0295127 A1 | 12/2011 | Sandler et al. |
| 2011/0300847 A1 | 12/2011 | Quy |
| 2011/0306846 A1 | 12/2011 | Osorio |
| 2011/0313484 A1 | 12/2011 | Hincapie Ordonez et al. |

FOREIGN PATENT DOCUMENTS

| | | |
|---|---|---|
| GB | 2 026 870 | 12/1982 |
| GB | 2 079 610 | 4/1983 |
| WO | WO-00/64336 | 6/2002 |
| WO | WO-2004/036377 A2 | 4/2004 |
| WO | WO-2005/007120 | 1/2005 |
| WO | WO-2005/053788 | 6/2005 |
| WO | WO-2005/067599 | 7/2005 |
| WO | WO-2006/050144 | 5/2006 |
| WO | WO-2006/122148 | 11/2006 |
| WO | WO-2006/134359 A1 | 12/2006 |
| WO | WO-2007/066343 | 6/2007 |
| WO | WO-2007/072425 | 11/2007 |
| WO | WO-2007/124126 | 11/2007 |
| WO | WO-2007/124190 | 11/2007 |
| WO | WO-2007/124192 | 11/2007 |
| WO | WO-2007/142523 | 12/2007 |
| WO | WO-2008/045597 A1 | 4/2008 |
| WO | WO-2011/126931 A1 | 10/2011 |

(56) References Cited

FOREIGN PATENT DOCUMENTS

OTHER PUBLICATIONS

Baevsky, R.M. et al., "Regulation of Autonomic Nervous System in Space and Magnetic Storms", Adv. Space Res., vol. 22, No. 2., pp. 227-234; 1998.

Baevsky, R.M., et al.; "Autonomic Cardiovascular and Respiratory Control During Prolonged Spaceflights Aboard the International Space Station," J. Applied Physiological, vol. 103, (2007) pp. 156-161.

Boon, P., et al.; "Vagus Nerve Stimulation for Epilepsy, Clinical Efficacy of Programmed and Magnet Stimulation," (2001); pp. 93-98.

Boon, Paul, et al.; "Programmed and Magnet-Induced Vagus Nerve Stimulation for Refractory Epilepsy," Journal of Clinical Neurophysiology vol. 18 No. 5; (2001); pp. 402-407.

Borovikova, L.V., et al.; "Vagus Nerve Stimulation Attenuates the Systemic Inflammatory Response to Endotoxin," Letters to Nature; vol. 405; (May 2000); pp. 458-462.

Brack, Kieran E., et al.; "Interaction Between Direct Sympathetic and Vagus Nerve Stimulation on Heart Rate in the Isolated Rabbit Heart," Experimental Physiology vol. 89, No. 1; pp. 128-139, 2004.

Chakravarthy, N., et al.; "Controlling Synchronization in a Neuron-Leve/ Population Model;" International Journal of Neural Systems, vol. 17, No. 2 (2007) pp. 123-138.

Apmkorea, "Leading PhotoPlethysmoGraphy Sensor Technology, Transmissive SpO2 PPG Sensor," found at: http://www.apmkr.com/spo2_oximeter_blood_sensor.htm.

Clark, K.B. et al, "Posttraining Electrical Stimulation of Vagal Afferents with Concomitant Vagal Efferent Inactivation Enhances Memory Storage Processes in the Rat", Neurobiology of Learning and Memory, vol. 70, 364-373, 1998.

Clinicaltrials.gov, "Exploring Biomarkers for Depression," found at: http://clinicaltrials.gov/ct2/show/ NCT01424111.

DeGiorgio et al., "Pilot Study of Trigeminal Nerve Stimulation (TNS) for Epilepsy: A Proof-of-Concept Trial," Epilepsia, 47(7):1213-1215, 2006.

DiGenarro, Giancarlo et al., "Ictal Heart Rate Increase Precedes EEG Discharge in Drug-Resistant Mesial Temporal Lobe Seizures," Clinical Neurophysioloqv, No. 115, 2004, pp. 1169-1177.

"Heart Rate Variability—Standards of Measurement, Physiological Interpretation, and Clinical Use" Circulation-Electrophysiology vol. 93, No. 5; http://circ.ahajournals.org/cgi/content-nw/full/93/5/1043/F3, printed on Sep. 10, 2013.

Elmpt, W.J.C., et al.; "A Model of Heart Rate Changes to Detect Seizures in Severe Epilepsy" Seizure vol. 15, (2006) pp. 366-375.

Frei, M.G., et al.; "Left Vagus Nerve Stimulation with the Neurocybernetic Prosthesis Has Complex Effects on Heart Rate and on Its Variability in Humans:" Epilepsia, vol. 42, No. 8 (2001); pp. 1007-1016.

George, M.S., et al.; "Vagus Nerve Stimulation: A New Tool for Brain Research and Therapy," Society of Biological Psychiatry vol. 47 (2000) pp. 287-295.

Hallowitz et al., "Effects of Vagal Volleys on Units of Intralaminar and Juxta/aminar Tha/amic Nuclei in Monkeys," Brain Research, vol. 130 (1977), pp. 271-286.

Henry, Thomas R.; "Therapeutic Mechanisms of Vague Name Stimulation;". Neurology, vol. 59 (Supp 4) (Sep. 2002), pp. S3-S14.

Iasemidis, L.D.; "Epileptic Seizure Prediction and Control" IEEE Transactions on Biomedical Engineering, vol. 50, No. 5 (May 2003); pp. 549-558.

Iasemidis; L.D., et al.; "Dynamical Resetting of the Human Brain at Epilepctic Seizures: Application of Nonlinear Dynamics and Global Optimization Techniques," IEEE Transactions on Biomedical Engineering, vol. 51, No. 3 (Mar. 2004); pp. 493-506.

Iasemidis; L.D., et al.; "Spatiotemporal Transition to Epileptic Seizures: A Nonlinear Dynamical Analysis of Scalp and Intracranial EEG Recordings," Spatiotemporal Models in Biological and Artificial Systems; F.L. Silva et al. (Eds.) IOS Press, 1997; pp. 81-88.

Kautzner, J., et al.; "Utility of Short-Term Heart Rate Variability for Prediction of Sudden Cardiac Death After Acute Myocardial Infarction" Acta Univ. Palacki. Olomuc., Fae. Med., vol. 141 (1998) pp. 69-73.

Koenig, S.A., et al.; "Vagus Nerve Stimulation Improves Severely Impaired Heart Rate Variability in a Patient with Lennox-Gastaut-Syndrome" Seizure (2007) Article in Press—YSEIZ-1305; pp. 1-4.

Koo, B., "EEG Changes With Vagus Nerve Stimulation" Journal of Clinical Neurophysiology, vol. 18 No. 5 (Sep. 2001); pp. 434-441.

Krittayaphong, M.D., et al.; "Heart Rate Variability in Patients with Coronary Artery Disease: Differences in Patients with Higher and Lower Depression Scores" Psychosomatic Medicine vol. 59 (1997) pp. 231-235.

Leutmezer, F., et al.; "Electrocardiographic Changes at the Onset of Epileptic Seizures," Epilepsia, vol. 44, No. 3; (2003); pp. 348-354.

Lewis, M.E., et al.; "Vagus Nerve Stimulation Decreases Left Ventricular Contractility in Vivo in the Human and Pig Heart" The Journal of Physiology vol. 534, No. 2, (2001) pp. 547-552.

Li, M., et al.; "Vagal Nerve Stimulation Markedly Improves Long-Term Survival After Chronic Heart Failure in Rats," Circulation (Jan. 2004) pp. 120-124.

Licht, C.M.M.; Association Between Major Depressive Disorder and Heart Rate Variability in the Netherlands Study of Depression and Anxiety (NESDA); Arch. Gen Psychiatry, vol. 65, No. 12 (Dec. 2008); pp. 1358-1367.

Lockard et al., "Feasibility and Safety of Vagal Stimulation in Monkey Model," Epilepsia, vol. 31 (Supp. 2) 1990, pp. S20-S26.

Long, Teresa J. et al., "Effectiveness of Heart Rate Seizure Detection Compared to EEG in an Epilepsy MoitoringUnit (EMU)," abstract of AES Proceedin s, Epilepsia, vol. 40, Suppl. 7, 1999, p. 174.

McClintock, P., "Can Noise Actually Boost Brain Power" Physics World Jul. 2002; pp. 20-21.

Method of Evaluation of the Functional State Regulatory Body of Biological Object; Russia Patent Application No. RU 2103911, published Nov. 8, 1993 to Baevsky et al.

Mori, T., et al.; "Noise-Induced Entrainment and Stochastic Resonance in Human Brain Waves" Physical Review Letters vol. 88, No. 21 (2002); pp. 218101-1-218101-4.

Mormann, F., "Seizure prediction: the long and winding road," Brain 130 (2007), 314-333.

Mousavi et al., Effects of Selected Aerobic Exercises on the Depression and Concentrations of Plasma Serotonin in the Depressed Female, Research Gate, Jan. 2012.

Neurosigma, "Trigeminal Nerve Stimulation (TNS)," found at: http://www.neurosigma.com/tns.html.

Nouri, M.D.; "Epilepsy and the Autonomic Nervous System" emedicine (updated May 5, 2006); pp. 1-14; http://www.emedicine.com/neuro/topic658.htm.

O'Donovan, Cormac A. et al., "Computerized Seizure Detection Based on Heart Rate Changes," abstract of AES Proceedings, Epilepsia, vol. 36, Suppl. 4, 1995, p. 7.

O'Regan, M.E., et al.; "Abnormalities in Cardiac and Respiratory Function Observed During Seizures in Childhood" Developmental Medicine & Child Neurlogy, vol. 47 (2005) pp. 4-9.

Osorio, Ivan et al, "An introduction to contingent (Closed-Loop) Brain Electrical Stimulation For Seizure Blockage, to Ultra-Short-Term Clinical Trials, and to Multidimensional Statistical Analysis of Therapeutic Efficacy," Journal of Clinical Neurophysioloqv, vol. 18, No. 6, pp. 533-544, 2001.

Osorio, Ivan et al., "Automated Seizure Abatement in Humans Using Electrical Stimulation," Annals of Neurology, vol. 57, No. 2, pp. 258-268, 2005.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "Complex Estimation of Adaptation Abilities of the Organism in Children Using the Indices of Responsiveness of the Cardiovascular System and Characteristics of EEG" Neurophysiology vol. 38, No. 1 (2006); pp. 63-74.

PR Newswire, "NeuroSigma at the 2011 American Epilepsy Society Annual Meeting and Introduce External Trigeminal Nerve Stimulation-the USB Port to le Brain," Nov. 29, 2011, found at: http://www.

(56) References Cited

OTHER PUBLICATIONS prnewswire.com/ news-releases/neurosigma-to-exhibit-at-the-2011-american-epilepsy-society-annual-meeting.

Robinson, Stephen E et al., "Heart Rate Variability Changes As Predictor of Response to Vagal Nerve Stimulation Therapy for Epilepsy," abstract of AES Proceedinqs,Epilepsia, vol. 40, Suppl. 7, 1999, p. 147.

Rugg-Gunn, F.J., et al.; "Cardiac Arrhythmias in Focal Epilepsy: a Prospective Long-Term Study" www.thelancet.com vol. 364 (2004) pp. 2212-2219.

Sajadieh, A., et al.; "Increased Heart Rate and Reduced Heart-Rte Variability are Associated with Subclinical Inflammation in Middle-Aged and Elderly Subjects with no. Apparent Heart Disease" European Heart Journal vol. 25, (2004); pp. 363-370.

Sandercock et al., Effect of Exercise on Heart Rate Variability: inferences from Meta-Analysis, Med Sci Sports Exerc., p. 433-439,2005.

Schernthaner, C., et al.; "Autonomic Epilepsy—The Influence of Epileptic Discharges on Heart Rate and Rhythm" The Middle European Journal of Medicine vol. 111, No. 10 (1999) pp. 392-401.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Terry et al.; The Implantable Neurocybernetic Prosthesis System, Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Umetani, M.D., et al.; "Twenty-Four Hour Time Domain Heart Rate Variability and Heart Rate: Relations to Age and Gender Over Nince Decades" JACC vol. 31, No. 3; (Mar. 1998); pp. 593-601.

Bachman, D.,S. et al.; "Effects of Vagal Volleys and Serotonin on Units of Cingulate Cortex in Monkeys," Brain Research, vol. 130 (1977). pp. 253-269.

Vonck, K., et al. "The Mechanism of Action of Vagus Nerve Stimulation for Refractory Epilepsy the Current Status", Journal of Neurophysiology, vol. 18 No. 5 (2001), pp. 394-401.

Weil, Sabine et al, "Heart Hate Increase in Otherwise Subclnical seizures is Different in Temporal Versus Extratemporal Seizure Onset: Support for Temporal Lobe Automatic Influence," Epileptic Disord., vol. 7, No. 3, Sep. 2005, pp. 199-204.

Wikipedia, "Photoplethysmogram," found at: http://en.wikipedia.org/wiki/Photoplethysmogram.

Woodbury, et al., "Vagal Stimulation Reduces the Severity of Maximal Electroshock Seizures in Intact Rats. Use ofa Cuff Electrode for Stimulating and Recording"; Pacing and Clinical Electrophysiology, vol. 14 (Jan. 1991), pp. 94-107.

Zabara, J. "Inhibition of Experimental Seizures in Canines by Repetivie Vagal Stimulation" Epilepsia vol. 33, No. 6 (1992); pp. 1005-1012.

Zabara, J., et al.; "Neural Control of Circulation /" The Physiologist, vol. 28 No. 4 (1985); 1 page.

Zabara, J., et al.; "Neuroinhibition in the Regulation of Emesis" Space Life Sciences, vol. 3 (1972) pp. 282-292.

Zabara, J.; "Neuroinhibition ofXylaine Induced Emesis" Pharmacology & Toxicology, vol. 63 (1988) pp. 70-74.

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, oas. 847-854.

* cited by examiner

METHODS AND SYSTEMS TO DIAGNOSE DEPRESSION

CROSS REFERENCE TO RELATED APPLICATION

This patent application is a continuation of U.S. patent application Ser. No. 13/746,478, filed Jan. 22, 2013, which has issued as U.S. Pat. No. 10,220,211, and which is incorporated herein by reference in its entirety.

FIELD OF THE DISCLOSURE

The present disclosure is generally related to cranial nerve stimulation to treat depression disorders.

BACKGROUND

The human nervous system includes the brain and the spinal cord, collectively known as the central nervous system. The central nervous system includes nerve fibers that transmit nerve signals to, from, and within the brain and spinal cord. The network of nerves in the remaining portions of the human body forms the peripheral nervous system. A system of peripheral nerves connects directly to the brain to control various brain functions, such as vision, eye movement, hearing, facial movement, and feeling. Another system of peripheral nerves, known as the autonomic nervous system, controls autonomic functions. Autonomic functions include blood pressure, body temperature, heartbeat, blood vessel diameter control, intestinal movements, actions of many internal organs, and other body activities and functions that occur without voluntary control.

Neurological disorders may affect the human nervous system. Some neurological disorders (e.g., epilepsy and depression) may be monitored, treated with medication, with neurostimulation, or a combination thereof. Neurostimulation may include electrical stimulation of the nervous system. Forms of neurostimulation may include cranial nerve stimulation, such as vagus nerve stimulation (VNS) or trigeminal nerve stimulation (TNS). A device that applies TNS may be configured to apply subcutaneous TNS, transcutaneous TNS, or both. VNS and subcutaneous TNS may require surgical implantation of electrodes in a patient. Transcutaneous TNS may be implemented by external electrodes coupled to the patient in one or more regions where nerve branches are near the surface of the skin.

SUMMARY

A medical device may be used to implement cranial nerve stimulation (CNS) to treat depression disorders (e.g., major depressive disorder, dysthymia, seasonal affective disorder, and postpartum depression). CNS may include TNS, VNS, stimulation of other cranial nerves, or a combination thereof. The medical device may be configured to apply open-loop therapy (e.g., a scheduled therapy or treatment) to a patient. The open-loop therapy may inhibit the occurrence of depression episodes in the patient, reduce duration of depression episodes that do occur, reduce intensity of depression episodes that do occur, or combinations thereof. The medical device may also be configured to implement closed-loop therapy (e.g., an episode therapy or treatment) when processed sensor data indicates onset of a depression episode. The closed-loop therapy may limit depression episode duration, depression episode severity, or both. Open-loop therapy, closed-loop therapy, or both, may include CNS, administration of medicine, other treatment, or combinations thereof.

In a particular embodiment, a system includes a first sensor configured to provide first sensor data corresponding to a first body parameter value for a patient. The system also includes a second sensor configured to provide second sensor data corresponding to a second body parameter value for the patient. The system further includes a processing unit configured to receive the first sensor data and the second sensor data. The processing unit includes a processor configured to determine a first depression-indicative value based on the first body parameter value and a second-depression indicative value based on the second body parameter value. The processor is also configured to determine a depression detection value as a function of a first weight applied to the first depression-indicative value and a second weight applied to the second depression-indicative value. The processor is further configured to determine a depression state based at least in part on a comparison of the depression detection value to one or more threshold values.

In a particular embodiment, a method includes receiving sensor data at a processor from sensors of an external medical device. The sensor data corresponds to at least a first body parameter value for a patient and a second body parameter value for the patient. The method includes determining, via the processor, a first depression-indicative value based on the first body parameter value and a second depression-indicative value based on the second body parameter value. The method includes determining, via the processor, a depression detection value as a function of a first weight applied to the first depression-indicative value and a second weight applied to the second depression-indicative value. The method includes determining, via the processor, a depression state based at least in part on a comparison of the depression detection value to one or more threshold values. The method may also include automatically adjusting, via the processor, at least one of the first weight and the second weight in response to an indication contradicting the depression state.

In a particular embodiment, a non-transitory computer-readable medium includes instructions executable by a processor. The instructions may be executable by the processor to receive sensor data from sensors of an external medical device. The sensor data corresponds to at least a first body parameter value for the patient and a second body parameter value for the patient. The instructions may be executable by the processor to determine a first depression-indicative value based on the first body parameter value and a second depression-indicative value based on the second body parameter value. The instructions may be executable by the processor to determine a depression detection value as a function of a first weight applied to the first depression-indicative value and a second weight applied to the second depression-indicative value. At least a value for the first weight depends on one or more values determined from the sensor data. The instructions may also be executable by the processor to determine a depression state based at least in part on a comparison of the depression detection value to one or more threshold values.

DETAILED DESCRIPTION

A medical device system may be used to provide cranial nerve stimulation (CNS) to a patient to treat a depression disorder. The CNS may include trigeminal nerve stimulation, vagus nerve stimulation, stimulation of other cranial nerves, or combinations thereof. The medical device system may enable the application of open-loop therapy to the patient. The open-loop therapy may reduce depression episode frequency, depression episode intensity, depression episode duration, or combinations thereof, for the patient. The medical device system may also enable the application of closed-loop therapy. Closed-loop therapy may be initiated via the medical device system when a depression state determined from sensor data collected by the medical device system indicates onset of a depression episode. The closed-loop therapy may limit depression episode duration, depression episode intensity, or both, for the patient. Open-loop therapy, closed-loop therapy, or both, may include CNS signals, medicine delivery, other treatment, or combinations thereof.

The medical device system may include a medical device and a processing unit that are external to the patient. The medical device may include one or more sensors and one or more pairs of electrodes that enable application of CNS (e.g., trigeminal nerve stimulation). The processing unit may initiate scheduled CNS signals at appropriate times. The processing unit may also initiate closed-loop therapy when a depression state determined from collected sensor data indicates depression episode onset. The processing unit may cease the closed-loop therapy when the depression state determined from the collected sensor data indicates depression offset.

Figure 1:
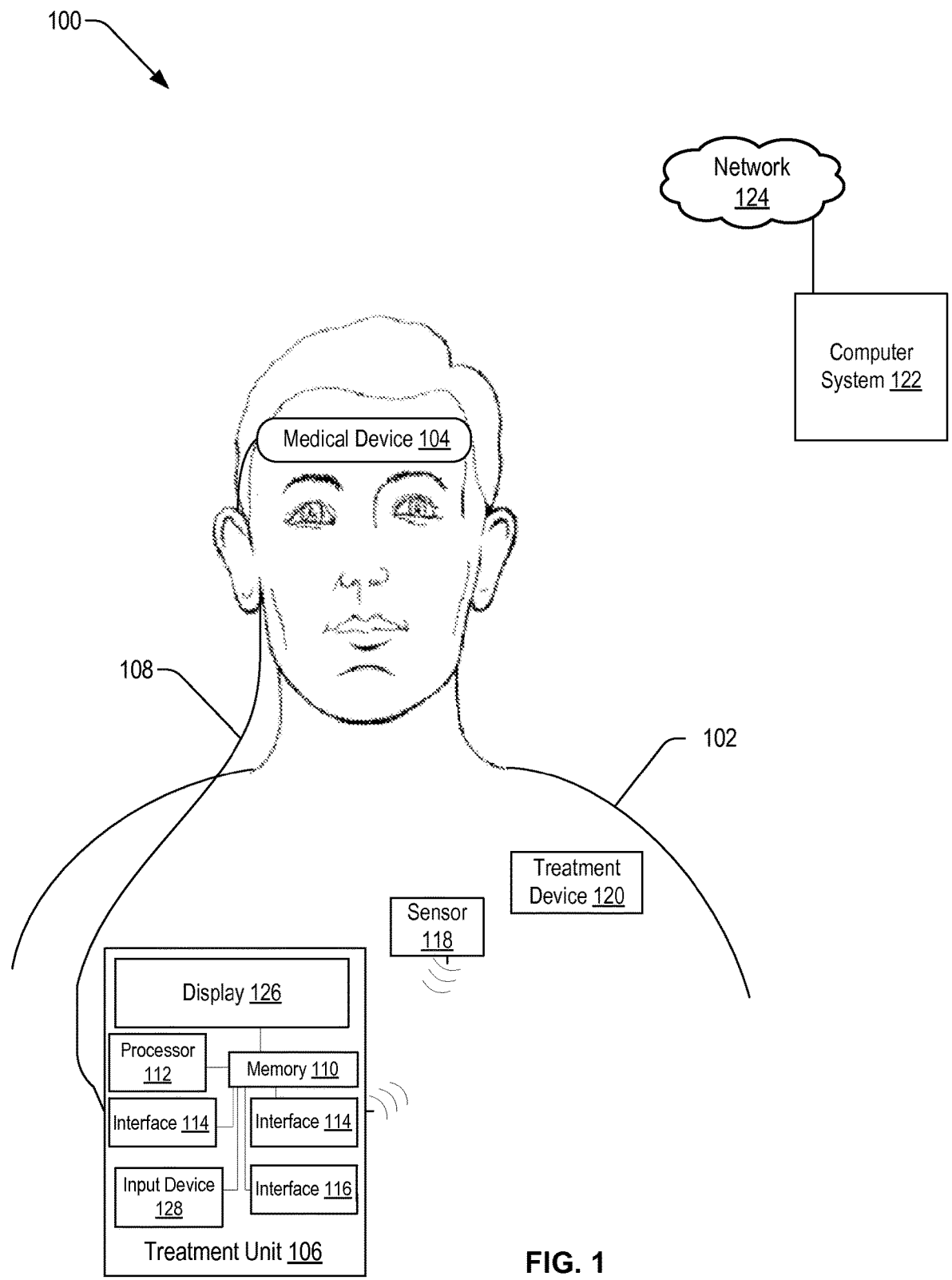
FIG. 1 is a block diagram of an embodiment of a medical device system that uses cranial nerve stimulation (CNS) to treat a depression disorder.

FIG. 1 is a representation of a particular embodiment of a medical device system 100 that uses CNS to treat a patient 102 that has been diagnosed as having a depression disorder (e.g., major depressive disorder, dysthymia, seasonal affective disorder, and postpartum depression). The medical device system 100 may include a medical device 104 that attaches to the patient 102 and a processing unit 106. In an embodiment, the medical device 104 may include one or more adhesive patches that attach to the patient 102. In other embodiments, the medical device 104 may be attached to an article of clothing (e.g., a headband, scarf, hat, or other clothing item) that the patient 102 wears. The medical device 104, the article of clothing, or both may include one or more indicators that facilitate correct placement of the medical device 104 on the patient 102.

The medical device 104 may include one or more treatment devices, sensors, or combinations thereof for treating and monitoring the patient 102. For example, the medical device 104 may include one or more pairs of electrodes that enable application of trigeminal nerve stimulation (TNS) and collection of skin conductance data. The medical device 104 may also include other sensors such as, but not limited to, a skin temperature sensor, a heart rate sensor, an oximeter, an accelerometer, a pedometer, or combinations thereof.

The medical device 104 may communicate with the processing unit 106. Sensors of the medical device 104 may send sensor data to the processing unit 106. The medical device 104 may also receive CNS signals from the processing unit 106 that enable one or more pairs of electrodes of the medical device 104 to apply CNS to the patient 102.

Communications between the medical device 104 and the processing unit 106 may include wireless communications, wired communications, or combinations thereof. In an embodiment, the processing unit 106 and the medical device 104 are an integrated unit and communications between the processing unit 106 and the medical device 104 are accommodated by internal connections in the integrated unit. In another embodiment, at least a portion of the processing unit 106 and the medical device 104 are an integrated unit and communications between the processing unit 106 and the medical device 104 are accommodated by internal connections in the integrated unit. In another embodiment, at least a portion of communications between the medical device 104 and the processing unit 106 are accommodated via a wired connection 108. In another embodiment, at least a portion of communications between the medical device 104 and the processing unit 106 are accommodated via wireless communications (e.g. by radio frequency communications, by infrared communications, by internet communications, or combinations thereof).

The medical device 104, the processing unit 106, or both may include one or more batteries, capacitors, other power supplies, or combinations thereof, to power the treatment devices and the sensors of the medical device 104 and to power the processing unit 106. Batteries for the medical device 104 and the processing unit 106 may be rechargeable batteries, disposable batteries, or combinations thereof. The medical device 104, the processing unit 106, or both may be coupled to another type of power supply (e.g., an electromagnetic signal to enable inductive powering or an electrical outlet) to provide operational power, power to recharge batteries, capacitive charging, or combinations thereof.

The processing unit 106 may include a processor 110, a memory 112, and interfaces 114, 116. The processor 110 may be a single processor of the processing unit 106 or multiple processors of the processing unit 106. The memory 112 may include instructions executable by the processor 110 to operate the medical device system 100. The interfaces 114, 116 may enable the processing unit 106 to communicate with other devices. One or more device interfaces 114 may enable wired or wireless communication directly with certain devices (e.g., the medical device 104, a sensor 118, a treatment device 120, a second treatment device 130, and a computer system 122). One or more network interfaces 116 may enable the processing unit 106 to communicate with certain devices (e.g., the medical device 104, the sensor 118, the treatment device 120, a second treatment device 130, and the computer system 122) via a network 124. The network 124 may be a local area network, the internet, a telecommunication network, other communication network, or combinations thereof. For example, the processing unit 106 may send a treatment initiation signal from the interface 116 to a uniform resource identifier (URI) associated with the treatment device 120 via the network 124.

The processing unit 106 may also include a display 126, one or more input devices 128 (e.g., input buttons, a touch pad, a keyboard, a key pad, etc.), one or more output devices (e.g., speakers, vibration devices, etc.), other components, or combinations thereof. In some embodiments, the display 126 may be an input device of the one or more input devices 128 (i.e., a touch screen). The display 126, the one or more input devices 128, and the one or more output devices may facilitate communications and delivery of notifications between the processing unit 106, the patient 102, and healthcare provider personnel.

The processor 110 of the processing unit 106 may request sensor data from one or more sensors. Alternately, one or more sensors may automatically send sensor data to the processor 110. The processing unit 106 may receive sensor data from the medical device 104 and from one or more other sensors. For example, the processing unit 106 may receive sensor data from the medical device 104 and from the sensor 118. The sensor 118 may be a respiration sensor, a sphygmomanometer (i.e., a blood pressure meter), a pedometer, another sensor, or combinations thereof that provides sensor data to the processing unit 106 wirelessly or by a wired connection. In an embodiment, the sensor 118 may be coupled to the processing unit 106, the patient 102, or both, substantially during a time period when the medical device 104 is coupled to the processing unit 106 and the patient 102. In other embodiments, the sensor 118 may be coupled to the processing unit 106, the patient 102, or both, for selected time periods. For example, the sensor 118 may be a sphygmomanometer that the patient 102 connects to the processing unit 106 during waking hours and disconnects when the patient 102 prepares to go to sleep. The sensor data may be received at the processing unit 106 as sensor data sets associated with particular times.

The processor 110 of the processing unit 106 may process received sensor data (e.g., data received from the sensors of the medical device 104, the sensor 118, or both). Processing the sensor data may include determining one or more values from the sensor data, saving the sensor data in the memory 112, saving determined values in the memory 112, sending the sensor data to the computer system 122, sending determined values to the computer system 122, or combinations thereof. The computer system 122 may be one or more computational devices associated with a healthcare provider of the patient 102. The determined values may be body parameter values, depression-indicative values, depression detection values, depression states, other values, or combinations thereof. Sensor data may be streamed to the computer system 122 or may be sent to the computer system 122 at selected times.

The processing unit 106 may send open-loop therapy signals to initiate open-loop therapy of the patient 102. The open-loop therapy signals may be sent at regular intervals beginning at particular times or beginning when processed sensor data indicates that one or more body parameter values are in particular ranges. The open-loop therapy may be CNS signals (e.g., trigeminal nerve stimulation signals, vagus nerve stimulation signals, or other stimulation signals for other cranial nerves), medicine delivery, or combinations thereof. The open-loop therapy may be determined based on one or more treatment regimens. Each treatment regimen may be associated with a set of treatment parameters. The treatment parameters may include, but are not limited to, treatment intensity (e.g., signal amplitude or medicine dosage), stimulation frequency (e.g., how often the open-loop therapy is to occur), pulse frequency of CNS signals, duty cycle of CNS signals, charge balance of CNS signals, stimulation location, stimulation direction, type of stimulation (e.g., CNS signals, medicine, or both), or combinations thereof. In some embodiments, medicine delivery may be instigated via a medicine pump. In other embodiments, the processing unit 106 may provide a visual notification, an audio notification, a haptic notification (e.g., a vibration), or combinations thereof, to inform the patient 102 that the patient should take medicine. Information (e.g., treatment parameters) that enables the processing unit 106 to send the open-loop therapy signals may be received by the processing unit 106 as input from the healthcare provider via the one or more input devices 128, by transmission from the computer system 122, or both. Appropriate authentication, such as user identification and a password, may be required to initiate open-loop therapy, change open-loop therapy, or stop open-loop therapy.

The open-loop therapy signals may include scheduled CNS signals to inhibit the occurrence of depression episodes in the patient, reduce duration of depression episodes that occur, reduce intensity of depression episodes that occur, or combinations thereof. The processing unit 106 may apply different scheduled CNS treatment regimens at different times. For example, the processing unit 106 may apply a first scheduled CNS treatment regimen of CNS signals during hours when the patient 102 is typically awake, and may apply a second regimen of scheduled CNS signals, or no CNS signals, during hours when the patient 102 is typically asleep. Instead of, or in addition to, basing various regimens on time, the processing unit 106 may base various regimens on processed sensor data. For example, one or more body parameter values for the patient 102 may indicate that the patient is awake and the processing unit 106 may apply the first scheduled CNS treatment regimen during such times. One or more of the body parameter values for the patient 102 may change to values that indicate that the patient 102 is in or is approaching a sleep state. The processing unit 106 may apply the second regimen of scheduled CNS signals, or no CNS signals, when the one or more of the body parameter values indicate that the patient 102 is in or is approaching the sleep state.

The processing unit 106 may enable application of closed-loop therapy in response to detection of depression onset. The depression onset may be determined by the processing unit 106 based on the sensor data. Alternately, the depression onset may be determined by the computer system 122 based on the sensor data. Cessation of the closed-loop therapy may occur in response to depression offset, which may indicate that a depression episode has substantially finished. The processing unit 106 may also be responsive to commands from the computer system 122 to cease the closed-loop therapy, the open-loop therapy, or both.

The closed-loop therapy may include closed-loop therapy CNS signals, may include treatment provided by one or more other treatment devices (e.g., by the treatment device 120, the second treatment device 130), or a combination thereof. In an embodiment, the closed-loop therapy may be one or more replacement CNS signals that replace scheduled CNS signals. In another embodiment, the closed-loop therapy includes adjusting at least one parameter of the scheduled CNS signals to be different than a corresponding parameter of the scheduled CNS signals. The parameters may include, but are not limited to, amplitude, polarity, frequency, pulse width, pulse period, duty cycle, charge balancing, and signal duration. Replacement CNS signals or the modified scheduled CNS signals may be stronger than the scheduled CNS signals (e.g., current amplitude of closed-loop therapy CNS signals may be greater than current amplitude of scheduled CNS signals).

In addition to, or in lieu of, sending closed-loop therapy CNS signals to the patient 102, the processing unit 106 may send treatment initiation signals to one or more second treatment devices. For example, the processing unit 106 may send a treatment initiation signal to the treatment device 120 and/or the second treatment device 130 when a determined depression state indicates onset of a depression episode. The treatment initiation signal may cause the treatment device 120 and/or the second treatment device 130 to provide closed-loop therapy to limit depression episode duration, depression episode severity, or both. The treatment device 120 may be a controller of a vagus nerve stimulation (VNS) system, a medicine delivery system, another device, or combinations thereof. When the treatment device 120 is the controller of the VNS system, the controller may instruct the VNS system to apply closed-loop therapy VNS signals to the patient 102. The VNS system may be surgically implanted in the patient 102. To extend the working life of the VNS system, to inhibit the patient from becoming accustomed to VNS treatment, for other reasons, or for combinations thereof, the VNS system may be used in conjunction with CNS provided by the medical device 104 to the patient 102. When the treatment device 120 is the medicine delivery system (e.g., a medicine pump), the treatment device 120 may deliver a dose or doses of medicine to the patient 102 in response to the treatment initiation signals. When the treatment device 120 is the medicine delivery system, the treatment device 120, the processing unit 106, or both may include safeguards that limit the amount of medicine that can be delivered to the patient 102 in a particular time period. The second treatment device 130 may be an external vagus nerve stimulation (VNS) device configured to externally couple to the auricular branch of the patient's vagus nerve located at the patient's ear.

The processing unit 106 may be operational in different modes. A first mode may enable the processing unit 106 to collect sensor data from the patient 102 without application of treatment to the patient 102. The sensor data may be used to determine initial values of variables used to determine a depression state of the patient 102. A second mode may enable the processing unit 106 to collect sensor data from the patient 102 and to apply open-loop therapy to the patient 102. A third mode may enable the processing unit 106 to collect sensor data from the patient 102, to apply open-loop therapy to the patient 102, and to apply closed-loop therapy to the patient 102 when a depression state determined from the data indicates onset of a depression episode. A fourth mode may enable the processing unit 106 to collect data from the patient 102 and to apply closed-loop therapy to the patient 102 when a depression state determined from the data indicates onset of a depression episode without applying open-loop therapy to the patient 102. The processing unit 106 may have fewer operational modes, additional operational modes, or different operational modes. A healthcare provider may be able to change the operational mode of the processing unit 106 via the one or more input devices 128, via transmission of a mode change instruction to the processing unit 106, or both. Appropriate authentication, such as user identification and a password, may be required to change the operational mode.

In an embodiment, the patient 102 may receive the medical device system 100 from the healthcare provider. The healthcare provider may provide the patient 102 with instructions on proper placement of the medical device 104, attachment of sensors (e.g., the medical device 104 and the sensor 118) to the processing unit 106 and the patient 102, user operation and maintenance of the processing unit 106, and other information pertaining to the medical device system 100. The processing unit 106 may be preprogrammed with instructions and data to enable operation of the medical device system 100.

The patient 102 may put on the medical device 104. The patient may connect the medical device 104 to the processing unit 106 and activate the medical device system 100. When the medical device system 100 is activated, diagnostic instructions in the memory 112 of the treatment device 120 may be executed by the processor 110 to ensure that the processing unit 106 is operating properly. At selected times, the processor 110 may execute the diagnostic instructions during operation of the medical device system 100 to ensure that the medical device system 100 continues to operate properly. Should the diagnostic instructions indicate a problem, the instructions may cause the processing unit 106 to generate a notification to the patient 102, the healthcare provider, or both. The notification may include audio output, visual output, haptic output (e.g., vibration of the processing unit 106), or combinations thereof. In an embodiment, the notification may include information presented via the display 126 of the processing unit 106 that identifies the problem. For example, the display 126 may show the statement "Please connect the medical device to the processing unit" if execution of the diagnostic instructions indicate no communication with the medical device 104. Depending on the detected problem, the medical device system 100 may also perform other actions, such as inhibiting application of treatment to the patient 102. When execution of the diagnostic instructions do not indicate problems with the medical device system 100, the medical device system 100 may collect sensor data, begin application of open-loop therapy to the patient 102, enable closed-loop therapy upon detection of a depression state that indicates onset of a depression episode, or combinations thereof depending on an operational mode of the processing unit 106.

The medical device 104 depicted in FIG. 1 is positioned above the eyes to enable stimulation of supraorbital branches of the trigeminal nerve. In other embodiments, the medical device 104 or portions of the medical device 104 may be configured to be positioned at another region of the face to stimulate other portions of the trigeminal nerve or another cranial nerve. For example, the medical device 104 may be, or may include, one or more patches that are configured to be placed near the nose to allow for stimulation of infraorbital branches of the trigeminal nerve.

A computation processor may be used to process sensor data received from sensors coupled to the processing unit 106 (e.g., the sensors of the medical device 104 and the sensor 118) to determine a depression state of the patient 102. The computational processor may be the processor 110 of the processing unit 106, may be a processor or processors of the computer system 122, may be a processor or processors of another device, or combinations thereof. The processing unit 106 may send the sensor data to the computation processor as raw sensor data, processed sensor data, or both. For example, the processing unit 106 may receive skin conductivity data from one or more skin conductivity sensors of the medical device 104, and the processing unit 106 may send the received skin conductivity data to the computation processor without processing the data. In another example, the processing unit 106 may receive oximeter data from an oximeter of the medical device 104, and the processor 110 of the processing unit 106 may calculate a heart rate and/or blood oxygen saturation from the oximeter data. The processing unit 106 may send the heart rate, the blood oxygen saturation, or both to the computation processor instead of, or along with, the oximeter data.

The sensor data may be received by the computation processor in sensor data sets. Each sensor data set may be associated with a particular time (t). A sensor data set may be used to determine a depression state for the patient 102 at the particular time. Sensor data of a sensor data set may correspond to at least one body parameter value (PV(t)) for the patient 102. For example, sensor data of a sensor data set may include temperature data from a temperature sensor. The temperature data may correspond to skin temperature for the time associated with the sensor data set. Also, the sensor data may include oximeter data from the oximeter. The oximeter data may correspond to the heart rate of the patient and the blood oxygen saturation of the patient for the time associated with the sensor data set. Body parameter values may include, but are not limited to, skin temperature, skin conductance, heart rate, change in heart rate, blood oxygen saturation, acceleration, respiration rate, and values determined as combinations thereof.

A depression-indicative value (DV) for a particular body parameter value as a function of time may be calculated according to the equation:

$$DV_{PV}(t) = PV_{foreground}(t) / PV_{background}(t) \quad \text{(Eqn 1)}$$

where $PV_{foreground}(t)$ is a moving average of a body parameter value of interest, and $PV_{background}(t)$ is a background value of the body parameter value of interest.

The value for $PV_{foreground}(t)$ for many body parameter values may be calculated as a simple moving average using the equation:

$$PV_{foreground}(t) = \frac{1}{WS} \cdot \sum_{k=s}^{WS+s} PV(t-k) \quad \text{(Eqn 2)}$$

where WS is a window size of the moving average, and s is a step size.

Indications of depression episodes may occur gradually over relatively long time periods (e.g., hours, days, or longer). Because of the relatively long periods of time needed to indicate depression episodes, the step size may range from seconds to a few minutes. The window size may be one or more hours, one or more days, or longer.

For some body parameter values (e.g., for values that are vectors), a moving average of a summed root-mean-squares may be used instead of the simple moving average provided by Eqn 2. Values for $PV_{foreground}(f)$ that are moving averages of summed root-mean-squares may be calculated using the equation:

$$PV_{foreground}(t) = \quad \text{(Eqn 3)}$$
$$\frac{1}{WS} \sum_{k=s}^{WS+s} \sqrt{(PV_X(t-k))^2 + (PV_Y(t-k))^2 + (PV_Z(t-k))^2}$$

where $PV_X(t-k)$ is an X-axis component of the body parameter value, $PV_Y(t-k)$ is a Y-axis component of the body parameter value, and $PV_Z(t-k)$ is a Z-axis component of the body parameter value.

For example, acceleration data received from a 3-axis accelerometer may be passed through a bandpass filter (e.g., a 0.1 Hz to 20.0 Hz bandpass filter) to obtain dynamic components for each axis (i.e., $Acc_X$, $Acc_Y$, and $Acc_Z$). The $Acc_{foreground}(t)$ may be calculated as:

$$Acc_{foreground}(t) = \quad \text{(Eqn 4)}$$

-continued
$$\frac{1}{WS} \sum_{k=s}^{WS+s} \sqrt{(Acc_X(t-k))^2 + (Acc_Y(t-k))^2 + (Acc_Z(t-k))^2}$$

The value for $PV_{background}(t)$ may be calculated using the equation:

$$PV_{background}(t) = (1-FR) \cdot PV_{background}(t-s) + FR \cdot PV_{foreground}(t) \quad \text{(Eqn 5)}$$

where FR is a forgetting factor.

Values of FR for particular body parameter values may be related to how quickly the body parameter values are able to return to an initial state after step changes. FR values may be values applicable to the general public, values applicable to a subset of the general public (e.g., from people diagnosed as having a particular depression disorder), or values determined from sensor data for the patient 102.

In other embodiments, the depression-indicative value or the background value of the body parameter value of interest may be calculated using other equations. For example, in some embodiments, the value for $PV_{background}(t)$ may be a baseline value for the body parameter value for the window size. Baseline values may initially be values applicable to the general public, values applicable to a subset of the general public (e.g., from people diagnosed as having a particular depression disorder), or values determined from sensor data for the patient 102. The baseline values may indicate a healthy condition (i.e., when the patient 102 does not experience one or more depression episodes during a time period of the window size). Baseline values may be updated based on historical data collected via the medical device system 100. Different baseline values may be used for different times of day, for different states of the patient 102 (e.g., awake or asleep), or both. In some embodiments, depression-indicative values may be calculated for various window sizes (e.g., for an hour window, a day window, a week window, and a month window). For example, depression-indicative values for various window sizes may be calculated using the equation:

$$DV_{Time,PV}(t) = \frac{1}{(Time) \cdot PV_{Time,baseline}} \cdot \sum_{k=s}^{Time+s} PV(t-k) \quad \text{(Eqn 6)}$$

where Time is a selected window size.

A depression detection value (DDV) may be determined from two or more depression-indicative values for particular body parameter values. For example, the DDV may be a weighted sum of different depression-indicative values. Depression-indicative values corresponding to some body parameter values may be directly proportional to the DDV (e.g., skin temperature, skin conductivity, and heart rate) while depression-indicative values corresponding to other body parameter values (e.g., blood oxygen saturation, step readings from a pedometer, and acceleration) may be inversely proportional to the DDV. The depression detection value as a function of time may be calculated using the equations:

$$DDV(t) = \sum_i w_i DV_i(t) + \sum_j w_j \frac{1}{DV_j(t)} \quad \text{(Eqn 7)}$$

and $$\Sigma_i w_i + \Sigma_j w_j = 1 \qquad \text{(Eqn 8)}$$

where $w_i$ and $w_j$ are weights, values of i correspond to different body parameter values that have depression-indicative values that are directly proportional to the depression detection value, values of j correspond to different body parameter values that have depression-indicative values that are inversely proportional to the depression detection value, and values of $DV_i(t)$ and $DV_j(t)$ may be values calculated using Eqn 1, Eqn 6, or both.

In some embodiments, initial values of the weights may be based on sensor data obtained from the medical device system 100 for the patient 102, based on data from a patient population that have a condition similar to the patient 102, or based on other factors. In some embodiments, the initial values of the weights may be evenly distributed (e.g., if there are four weights, each weight may initially have a value of 0.25) or may be unevenly distributed. During use, the computation processor may adjust values of the weights to improve detection of depression onset and/or depression offset of depression episodes. For example, the computation processor may determine subsequent rules for the weights based on sensor data for the patient 102 and other data that indicates depression onsets and depression offsets. The other data may be based on input from the patient, based on analysis of historic data, based on data from other sensors, or combinations thereof.

As an example of the use of Eqn 7 and Eqn 8, the body parameter values may correspond to skin temperature (ST), skin conductivity (SC), heart rate (HR), blood oxygen saturation (SpO2), and acceleration (Acc). For these body parameter values, Eqn 7 and Eqn 8 become:

$$DDV(t) = w_{ST} \cdot DV_{ST}(t) + w_{SC} \cdot DV_{SC}(t) + w_{HR} \cdot DV_{HR}(t) + \frac{w_{SpO2}}{DV_{SpO2}(t)} + \frac{w_{Acc}}{DV_{Acc}(t)} \qquad \text{(Eqn 9)}$$

and $$w_{ST} + w_{SC} + w_{HR} - w_{SpO2} = w_{Acc} = 1 \qquad \text{(Eqn 10)}$$

Eqn 9 and Eqn 10 may be used to calculate depression detection values for a particular sensor data set.

Physical activity level, an increased resting heart rate, decreased heart rate variability, an increase in resting skin temperature, an increase in resting skin conductance, an increase in resting respiration rate, and a decrease in blood oxygen saturation level may correlate with onset of a depression episode, severity of a depression episode, or both. Data corresponding to physical activity may be provided by a pedometer, by a 3-axis accelerometer, by a heart rate monitor, by another type of sensor, or by combinations thereof. Sensor of the medical device 104, one or more sensors 118 coupled to the processing unit 106, or both, may provide sensor data used to determine physical activity level, resting heart rate, heart rate variability, skin temperature, skin conductance, respiration rate, blood oxygen saturation levels, and other body parameter values that may be used to determine a depression state of the patient 102. One or more depression-indicative values corresponding to physical activity level, resting heart rate, heart rate variability, resting skin temperature, resting skin conductance, resting respiration rate, and blood oxygen saturation level for one or more window sizes may be used as depression-indicative values in Eqn 7 to determine the depression detection value.

One or more weight factors may be zero and corresponding data may be omitted from calculations of depression-indicative values when the patient 102 is not in the resting state. Whether the patient 102 is in a resting state or an active state may be determined from sensor data from one or more sensors. For example, an indication that the patient 102 is not in the resting state may be that the heart rate of the patient 102 is sustained above a heart rate of 100 beats per minute for longer than a minute. Other indications that the patient 102 is in an active state may be provided by received pedometer data that indicates that the patient 102 is moving and accelerometer data that indicates that the patient 102 is active.

The computation processor may determine the depression detection value periodically (e.g., at intervals associated with a particular step size) based on sensor data received from the sensors coupled to the processing unit 106. The computation processor may determine a depression state for each step based at least in part on a comparison of the depression detection value for the step to one or more thresholds. The depression state may be indicated by a depression onset value, a depression offset value, or both. In an embodiment, the computation processor may calculate a depression onset value and a depression offset value based on a previous value of the depression onset, a previous value of the depression offset, and based on a comparison of the current depression detection value to one or more thresholds. The depression onset value and the depression offset value as a function of time may be determined according to the equations:

$$\begin{cases} on(t) = 0, & off(t) = 0; & \text{if } on(t-s) = 0, \\ & & off(t-s) = 0 \text{ and } DDV(t) < T_{on} \\ on(t) = t, & off(t) = 0; & \text{if } on(t-s) = 0, \\ & & off(t-s) = 0 \text{ and } DDV(t) \geq T_{on} \\ on(t) = NC, & off(t) = 0; & \text{if } on(t-s) \neq 0, \\ & & off(t-s) = 0 \text{ and } DDV(t) \geq T_{off} \\ on(t) = NC, & off(t) = t; & \text{if } on(t-s) \neq 0, \\ & & off(t-s) = 0 \text{ and } DDV(t) < T_{off} \\ on(t) = 0, & off(t) = 0; & \text{if } on(t-s) \neq 0, \\ & & off(t-s) \neq 0 \text{ and } DDV(t) < T_{off} \end{cases} \qquad \text{(Eqn 11)}$$

where t is the elapsed time,
s is the step size,
on(t) is the depression onset at time t,
off(t) is the depression offset at time t,
"NC" stands for "not changed,"
$T_{on}$ is the threshold value for depression onset, and
$T_{off}$ is the threshold value for depression offset.

Table 1 depicts example data generated during application of Eqn 11. As indicated in the first row of Table 1, the depression onset value (i.e., on(t)) and the depression offset value (i.e., off(t)) may initially be zero, which may indicate that no depression episode is occurring. Sensor data may be sent to the computation processor for an initial number of steps of the step size to enable the computation processor to determine an initial DDV(t) value. The time corresponding to the initial DDV(t) value is set as s. As indicated in the first row and the second row of Table 1, the initial DDV(t) value is less than the threshold for depression onset (i.e., $T_{on}$), and the values of the depression onset and the depression offset at the previous time (i.e., at time 0) are zero when the time is s. Since the values of the previous depression onset and the previous depression offset are zero, a comparison of DDV(t) to the threshold value for depression offset (i.e., $T_{off}$) is not needed. According to the first line of Eqn 11, the values of the depression onset and the depression offset at time s remain zero. Similarly, as indicated in the second row and the third row of Table 1, the DDV(t) value is less than the threshold for depression onset, and the values of the depression onset and the depression offset at the previous time (i.e., at time s) are zero when the time is 2s. According to the first line of Eqn 11, the values of the depression onset and the depression offset at time 2s remain zero.

TABLE 1

| Row # | t   | DDV(t) and $T_{on}$ comparison | DDV(t) and $T_{off}$ comparison | on(t) | off(t) |
|-------|-----|--------------------------------|----------------------------------|-------|--------|
| 1     | 0   |                                |                                  | 0     | 0      |
| 2     | s   | DDV(t) < $T_{on}$              | not needed                       | 0     | 0      |
| 3     | 2 s | DDV(t) < $T_{on}$              | not needed                       | 0     | 0      |
| 4     | 3 s | DDV(t) > $T_{on}$              | not needed                       | 3 s   | 0      |
| 5     | 4 s | not needed                     | DDV(t) > $T_{off}$               | 3 s   | 0      |
| 6     | 5 s | not needed                     | DDV(t) > $T_{off}$               | 3 s   | 0      |
| 7     | 6 s | not needed                     | DDV(t) < $T_{off}$               | 3 s   | 6 s    |
| 8     | 7 s | not needed                     | DDV(t) < $T_{off}$               | 0     | 0      |
| 9     | 8 s | DDV(t) < $T_{on}$              | not needed                       | 0     | 0      |

As indicated in the third row and the fourth row of Table 1, the DDV(t) value is greater than the threshold for depression onset, and the values of the depression onset and the depression offset at the previous time (i.e., at time 2s) are zero when the time is 3s. According to the second line of Eqn 11, the value of the depression onset at time 3s becomes 3s and the value of the depression offset at time 3s remains zero. Until the depression onset value is returned to zero, a comparison of DDV(t) to the threshold value for depression onset is not needed, but a comparison of DDV(t) to the threshold value for depression offset is needed. Because the depression onset value changed from zero to a non-zero value, the processing unit 106 may initiate closed-loop therapy, depending on an operational mode setting of the processing unit 106.

As indicated in the fourth row and the fifth row of Table 1, the DDV(t) value is greater than the threshold for depression offset, the value of the depression onset at the previous time (i.e., at time 3s) is not zero, and the value of the depression offset at the previous time is zero when the time is 4s. According to the third line of Eqn 11, the value of the depression onset at time 4s remains 3s and the value of the depression offset at time 4s remains zero. Similarly, as indicated in the fifth row and the sixth row of Table 1, the DDV(t) value is greater than the threshold for depression offset, the value of the depression onset at the previous time (i.e., at time 4s) is not zero, and the value of the depression offset at the previous time is zero when the time is 5s. According to the third line of Eqn 11, the value of the depression onset at time 5s remains 3s and the value of the depression offset at time 5s remains zero.

As indicated in the sixth row and the seventh row of Table 1, the DDV(t) value is less than the threshold for depression offset, the value of the depression onset at the previous time (i.e., at time 5s) is not zero, and the value of the depression offset at the previous time is zero when the time is 6s. According to the fourth line of Eqn 11, the value of the depression onset at time 6s remains 3s and the value of the depression offset at time 6s becomes 6s. Because the depression offset value changed from zero to a non-zero value, the processing unit 106 may cease closed-loop therapy, depending on a mode setting of the processing unit 106.

As indicated in the seventh row and the eighth row of Table 1, the DDV(t) value is less than the threshold for depression offset, the value of the depression onset at the previous time (i.e., at time 6s) is not zero, and the value of the depression offset at the previous time is not zero when the time is 7s. According to the fifth line of Eqn 11, the values of the depression onset and the depression offset at time 7s are reset to zero. As indicated in the eighth row and the ninth row of Table 1, the DDV(t) value is less than the threshold for depression onset and the values of the depression onset and the depression offset at the previous time (i.e., at time 7s) are zero when the time is 8s. According to the first line of Eqn 11, the values of the depression onset and the depression offset at time 8s remain zero.

In some embodiments, the depression detection value may be compared to one or more pre-depression episode thresholds to determine whether the depression detection value for the patient 102 is approaching a value that indicates depression onset. When the comparison of the depression detection value to the one or more pre-depression episode thresholds is satisfied, a notification may be sent to the processing unit 106, the healthcare provider, or both. The notification sent to the processing unit 106 may include a visual notification, an audio notification, a haptic notification, or combinations thereof. The notification sent to the processing unit 106 may inform the patient 102 that the patient 102 may be approaching a depressive state. The notification may provide the patient 102 with one or more suggested courses of action to inhibit the patient 102 from reaching the depressive state. The suggestions may include, but are not limited to, initiate exercise, interact with people, walk, initiate a conversation with a friend or acquaintance, or combinations thereof. The notification sent to the healthcare provider may include an electronic mail, a text, a telephone call, or another form of communication. The notification may inform the healthcare provider that the patient 102 may be approaching a depressive state. A representative of the healthcare provider may contact the patient 102 in response to the notification to inquire about the condition of the patient 102 and facilitate a course of action by the patient 102 that inhibits onset of or reduces severity of the depressive state.

In some embodiments, one or more values (e.g., body parameter values, moving averages of one or more body parameter values, or depression-indicative values corresponding to particular body parameter values) may provide reasonably reliable indications of depression onset, depression offset, or both. However, such values may provide some false indications of depression onset or depression offset. The one or more values may be used in conjunction with the depression detection value determined from Eqn 7 to determine depression onset values and depression offset values. The determined depression onset values and depression offset values may have fewer false indications than either depression onset values and depression offset values determined only from the one or more values or from depression onset values and depression offset values determined only from the depression detection values.

When a change in the depression state of the patient 102 indicates onset of a depression episode, the medical device system 100 may initiate closed-loop therapy to stop the depression episode, limit an intensity of the depression episode, limit a duration of the depression episode, or combinations thereof. In some embodiments, the closed-loop therapy may include CNS signals sent from the processing unit 106 to the medical device 104 to provide CNS to the patient 102. The closed-loop therapy CNS signals may be stronger than scheduled CNS signals applied to the patient 102 to inhibit the occurrence of a depression episode. The closed-loop therapy CNS signals may be based on determined depression episode detection values. For example, in a simple embodiment, only the stimulation current of scheduled CNS signals is adjusted to form the closed-loop therapy CNS signals.

$$I_{resp} = \begin{cases} I_{norm} \cdot DDV(t); & \text{if } I_{norm} \cdot DDV(t) < maxI_{resp} \text{ and} \\ & I_{norml} \cdot DDV(t) > minI_{resp} \\ maxI_{resp}; & \text{if } I_{norm} \cdot DDV(t) \geq maxI_{resp} \\ minI_{resp}; & \text{if } I_{norm} \cdot DDV(t) \leq maxI_{resp} \end{cases} \quad \text{(Eqn 12)}$$

Eqn 12 enables application of a response stimulation current that varies from a minimum stimulation current (e.g., a stimulation current equal to or above the scheduled stimulation current) to a maximum stimulation current depending on a determined value of the depression detection value. In other embodiments, other parameters of the scheduled CNS signals (e.g., signal polarity, pulse width, and pulse period) may be adjusted in lieu of or in conjunction with adjustment of the stimulation current. In other embodiments, the closed-loop stimulation may comprise micro-burst stimulation, electrical stimulation in combination with other forms of therapy (e.g., drug/medication delivery), stimulation of multiple cranial nerves (e.g., the vagus, trigeminal, hypoglossal, glossopharyngeal), stimulation of left and right cranial nerves, simultaneous or coordinated (e.g., interleaved) stimulation at multiple nerve sites, one or more signal parameters randomized within a range, or a combination thereof. Micro-burst stimulation may include a signal having 2-10 pulses per burst where the pulses are provided at a frequency in the range of 100-300 Hertz.

In some embodiments, additional thresholds may be provided to indicate the severity of the depression episode. For example, one or more threshold values beyond the onset threshold may be provided and may be compared to the depression detection value, DDV(t), to determine the severity of the depression episode being experienced. If the depression detection value triggers one or more of the threshold values, certain actions may be initiated. For example, the therapy may be modified by increasing the current amplitude per pulse, adjusting various stimulation parameters (e.g., frequency, duty-cycle, off-time, on-time, pulse width, number of pulses, inter-pulse interval), randomizing certain signal parameters within a range, providing other forms of therapy (e.g., drug/medication delivery), stimulating multiple cranial nerves (e.g., the vagus, trigeminal, hypoglossal, glossopharyngeal), stimulating left and right cranial nerves, providing simultaneous or coordinated (e.g., interleaved) stimulation at multiple nerve sites, or a combination thereof. In addition, once a threshold is triggered, the value needed to return to the previous state (the state before triggering the threshold) may be offset from the threshold value (hysteresis) to avoid switching between states too frequently. Warnings or notifications may also be provided to a physician, patient, caregiver, monitoring service, or a combination thereof, when the depression detection value triggers one or more of the thresholds.

In some embodiments, the processing unit 106 may configured to store and trend one or more of the body parameter values as a function of time and one or more trend thresholds. When the trend satisfies one or more of the trend thresholds, the processing unit 106 may be provide a recommendation to the patient or a caregiver to take one or more actions to inhibit the depression episode. Trending may also be applied to the one or more depression-indicative values and the depression detection values to monitor the patient's progress overtime.

Figure 2:
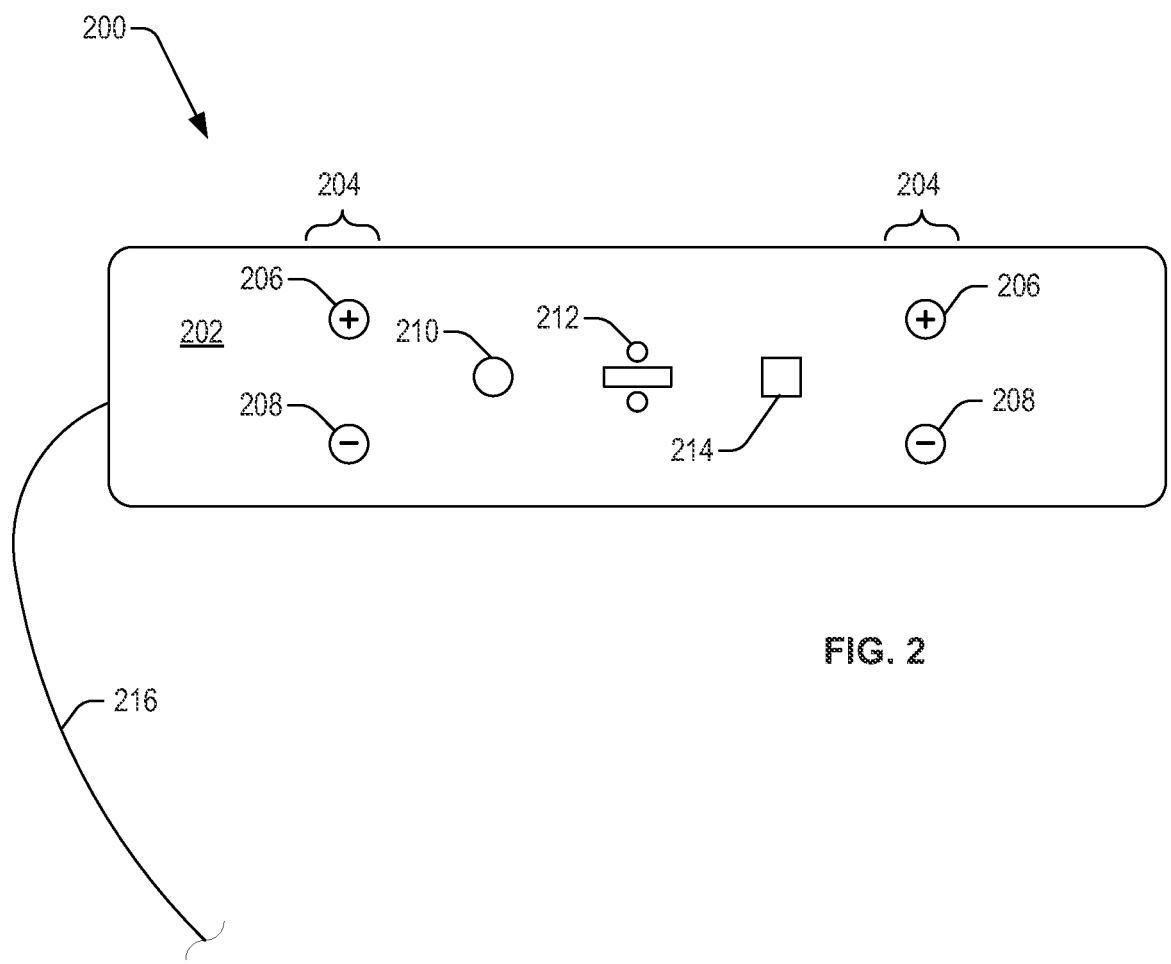
FIG. 2 is a block diagram of an external medical device of a medical device system that uses CNS signals to treat a depression disorder.

FIG. 2 is a schematic representation of a particular embodiment of an external medical device 200 to treat a patient that has been diagnosed as having a depression disorder (e.g., major depressive disorder, dysthymia, seasonal affective disorder, and postpartum depression). The medical device 200 may be the medical device 104 depicted in FIG. 1. The medical device 200 may include a base 202. The base 202 may be an adhesive patch that is placed against the skin of the patient. Alternately, the base 202 may be, or may be coupled to, an article of clothing that the patient wears. The article of clothing may be a headband, hat, scarf, other item, or a combination thereof.

The medical device 200 may include electrode pairs 204. Each electrode pair 204 may include a positive electrode 206 and a negative electrode 208. The electrode pairs 204 may enable application of CNS to the patient via a processing unit coupled to the medical device 200. The CNS may include transcutaneous TNS. Alternately, the CNS may include subcutaneous TNS via activation of one or more subcutaneously positioned electrode pairs by one or more of the electrode pairs 204. Alternatively, or in addition to enabling CNS, the electrode pairs 204 may enable the medical device 200 to collect skin conductance data. An electrically conductive contact gel or other electrically conductive material may be placed on contacts of the electrode pairs 204 before attachment of the medical device 200 to the patient to ensure good electrical contact between the electrode pairs 204 and the patient.

The medical device 200 may include a temperature sensor 210. The temperature sensor 210 may enable the medical device 200 to collect skin temperature data. In an embodiment, the temperature sensor 210 may be in contact with skin of the patient when the medical device 200 is attached to the patient. A thermally conductive gel or other thermally conductive material may be placed on the temperature sensor 210 before attachment of the medical device 200 to the patient to ensure good thermal contact between the temperature sensor 210 and the patient. In other embodiments, the temperature sensor 210 may be an optical temperature sensor or other type of temperature sensor that does not need to be in thermal contact with the patient.

The medical device 200 may include an oximeter 212. The oximeter 212 may enable the medical device 200 to collect oximeter data. The oximeter data may enable determination of patient blood oxygen saturation, patient heart rate, or both. The oximeter 212 may be a reflectance oximeter that detects reflections of light from a first light source at a first wavelength (e.g., a 905 nanometer (nm) light emitting diode (LED)) and a second light source at a second wavelength (e.g., a 660 nm LED). The oximeter 212 may be in contact with, or in proximity to, skin of the patient when the medical device 200 is attached to the patient.

The medical device 200 may also include a three axis accelerometer 214. The three axis accelerometer 214 may enable the medical device to collect acceleration data to the processing unit.

The medical device 200 may be communicatively coupled to a processing unit, such as the processing unit 106 depicted in FIG. 1. The medical device 200 may include a wired connection 216, one or more wireless connections, or both, to the processing unit to enable data from the electrode pairs 204, the temperature sensor 210, the oximeter 212, the three axis accelerometer 214, or a combination thereof, to be sent to the processing unit and to enable CNS signals received from the processing unit to be applied to the patient via the electrode pairs 204. The wired connection 216, one or more transceivers that enable wireless communication, or both, may be coupled to a bus that is electrically connected to the electrode pairs 204, the temperature sensor 210, the oximeter 212, the three axis accelerometer 214, or a combination thereof.

FIG. 2 depicts the medical device 200 with the electrode pairs 204 and three other sensors. In other embodiments, the medical device 200 may include fewer sensors, more sensors, or different sensors. For example, the medical device 200 may include a pedometer. In an embodiment, the medical device 200 does not include the oximeter 212. In this embodiment, the oximeter data may be provided by a transmittance oximeter or reflectance oximeter attached to the patient and communicatively coupled to the processing unit.

Figure 3:
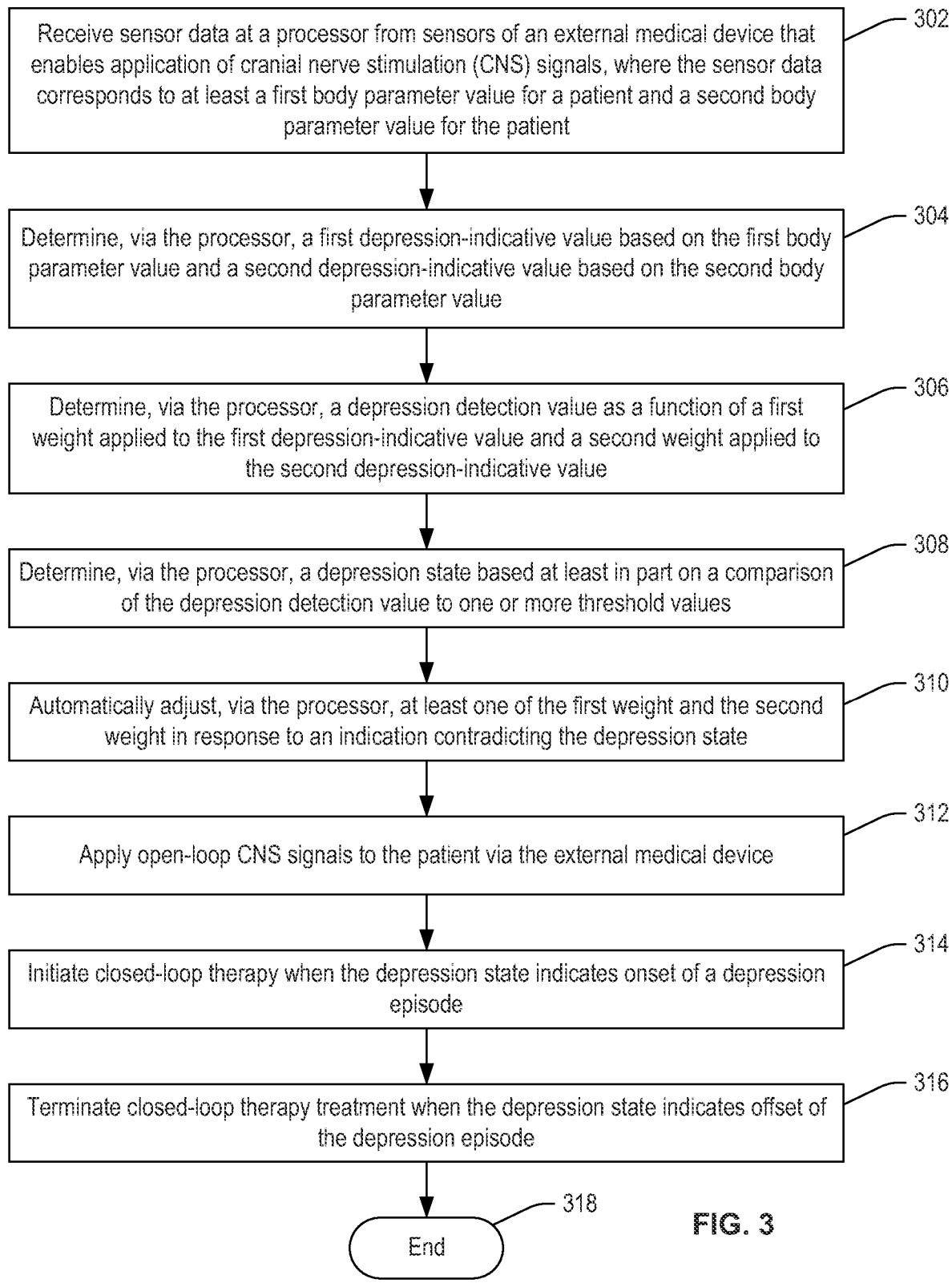
FIG. 3 is a flow chart of a first particular embodiment of a method of use of sensor data from a medical device that enables application of CNS signals to treat a depression disorder.

FIG. 3 is a flow chart of a first particular embodiment of a method of using cranial nerve stimulation (CNS) to treat a patient diagnosed with a depression disorder (e.g., major depressive disorder, dysthymia, seasonal affective disorder, and postpartum depression). The CNS may include trigeminal nerve stimulation, vagus nerve stimulation, stimulation of other cranial nerves, or combinations thereof. The CNS may be applied by an external medical device coupled to a patient (e.g., the medical device system 100 depicted in FIG. 1), an implanted medical device, or a combination thereof. In an embodiment, the method may be performed by a processor. The processor may be the processor of the external medical device or the processor of a device that receives the sensor data from the external medical device (e.g., the processor of a computer system associated with a healthcare provider). At 302, sensor data is received at the processor from sensors of the external medical device that enables application of CNS signals to the patient. The sensor data corresponds to at least a first body parameter value for the patient and a second body parameter value for the patient. The sensor data may be received as sensor data sets. Each sensor data set may correspond to a particular time and may include data associated with sensors of the external medical device. The sensors may include a temperature sensor, a conductivity sensor, an oximeter, a three axis accelerometer, a respiration sensor, a blood pressure sensor, a pedometer, other sensors, or combinations thereof.

The sensor data may include body parameter values or may enable the processor to calculate body parameter values corresponding to particular sensor data. For each sensor data set, the processor may store a time associated with the sensor data, the sensor data, values calculated based on the sensor data, or combinations thereof, as historic data. The values may include body parameter values, moving averages of body parameter values, change rates of body parameter values based on one or more previous sensor data sets, depression-indicative values, depression detection values, values associated with a depression state, or any combination thereof.

A first depression-indicative value based on the first body parameter value and a second depression-indicative value based on the second body parameter value may be determined by the processor, at 304. For example, the first depression-indicative value and the second depression-indicative value may be determined via application of Eqn 1 and Eqn 6.

A depression detection value may be determined by the processor, at 306. For example, the depression detection value may be determined as a function of a first weight applied to the first depression-indicative value and a second weight applied to the second depression-indicative value. The processor may determine the depression detection value by application of Eqn 7 and Eqn 8.

A depression state may be determined by the processor based at least in part on a comparison of the depression detection value to one or more threshold values, at 308. The one or more threshold values may include a depression onset threshold, a depression offset threshold, or both. In some embodiments, the depression onset threshold is the same as the depression offset threshold. The depression state may include a depression onset value and a depression offset value. The depression onset value and the depression offset value of the depression state may be calculated using Eqn 11.

In an embodiment, the depression onset value and the depression offset value may initially be zero, indicating that no depression episode is occurring. When a comparison of the depression detection value to the depression onset threshold is satisfied (e.g., the depression detection value is greater than or equal to the depression onset threshold), the depression onset value may be set to the time associated with the data set. When the depression onset value is not zero, the depression onset value may indicate the onset time of a depression episode. The value of the depression onset value may remain at that value until a comparison of depression detection values of two consecutive subsequent data sets to the depression offset threshold is satisfied (e.g., the depression detection values calculated from two consecutive sensor data sets are less than the depression offset threshold). The value of the depression offset value may be changed to a time associated with the first sensor data set of the two consecutive data sets to indicate a time when the depression episode is considered to be finished. The values of the depression onset value and the depression offset value may be both reset to zero in response to the depression detection value calculated from the second sensor data set satisfying the depression offset threshold.

In some embodiments, the external medical device may be configured to receive patient input. The medical device may provide an indication of when a change in the determined depression state occurs. The indication may be a visual indication, an audio indication, a vibrational indication, or combinations thereof. The patient may provide user input that indicates whether the patient agrees with the indication. For example, the processor may determine that a change in the depression onset value indicates onset of a depression episode at 3:05 p.m. on a particular day and a corresponding depression offset value at 5:30 p.m. on the particular day. At 5:35 p.m. on the particular day or at some other time, the processor may provide the notification to the patient and query the patient regarding whether the patient agrees that a depression episode occurred in the time frame between 3:05 and 5:30. User input in response to the query may be stored as patient input data. In some embodiments, the patient may be asked to keep track of onsets and offsets of depression episodes. The data kept by the patient may be entered into a computer and transmitted to the processor as patient input data.

The processor, another computing system, or both may be used to analyze historic data and patient input data for a particular time period. The time period may be a number of a week, a month, or other time period. A presentation of values obtained from the historic data as a function of time along with patient input data that indicates depression episode occurrences may be reviewed by one or more healthcare professionals, the patient, or both. The presentation may include graphs, charts, tabulated data, other formats of data presentation, or combinations thereof. Depression input may be received from one or more people reviewing the presentation. The depression input may indicate when depression onsets and depression offsets occurred based on the historic data.

The depression input may be sent to or received by the processor. The depression input may be compared by the processor to depression states determined by the processor to determine indications from the depression input that agree with or contradict the depression onset values and the depression offset values of the depression states determined by the processor. In response to an indication that contradicts a depression state determined by the processor, the processor may automatically adjust at least one of the first weight and the second weight, at 310. Adjustment of at least one of the first weight and the second weight may enable determined values of the depression state to more closely conform to the depression states indicated by the depression input. For example, depression input compared with determined depression states when the body parameter values are in certain ranges may indicate about 50% agreement regarding depression onset when the values of the first weight and the second weight are each at 0.25. At least one other weight factor allows the sum of all of the weight factors to add up to one, as in Eqn 8. Calculations performed by the processor may adjust the first weight to 0.7 and the second weight to 0.15 when the particular body parameter values are in the certain ranges to improve agreement between the determined depression states and the corresponding depression input of about 80%. The processor may perform statistical analysis, may determine depression states using various values for the first weight and the second weight, may employ other techniques, or may use combinations thereof, to determine the values of the first weight, the second weight, and other weights used to determine the depression states. After the weights are adjusted, the new weights may be used to determine subsequent depression states (e.g., depression onset values, depression offset values, or both).

Scheduled CNS signals may be applied to the patient via the external medical device, at 312. Scheduled CNS may inhibit the occurrence of depression episodes in the patient. Closed-loop therapy may be applied to the patient via the external medical device upon determination of a depression state that indicates depression onset, at 314. The closed-loop therapy may limit depression episode duration, depression episode severity, or both. The closed-loop therapy may include CNS signals, activation of a medicine delivery system, other treatment option, or combinations thereof.

In an embodiment, the closed-loop therapy may include one or more CNS signals that replace one or more scheduled CNS signals. In another embodiment, the closed-loop therapy includes adjusting at least one parameter of the one or more CNS signals to be different than a corresponding parameter of the scheduled CNS signals. The parameters may include, but are not limited to, amplitude, polarity, frequency, pulse width, pulse period, duty cycle, charge balancing, and signal duration. The CNS signals used for closed-loop therapy may be stronger than the scheduled CNS signals. For example, the at least one parameter may be stimulation current amplitude. The stimulation current amplitude may be adjusted between a minimum stimulation current amplitude and a maximum current stimulation amplitude based on a depression detection value calculated from a most recently received sensor data set. The closed-loop therapy may abort a depression episode or reduce depression episode intensity, depression episode duration, or both. Closed-loop therapy may be terminated when the depression state indicates offset of the depression episode, at 316. The method may end, at 318.

Figure 4:
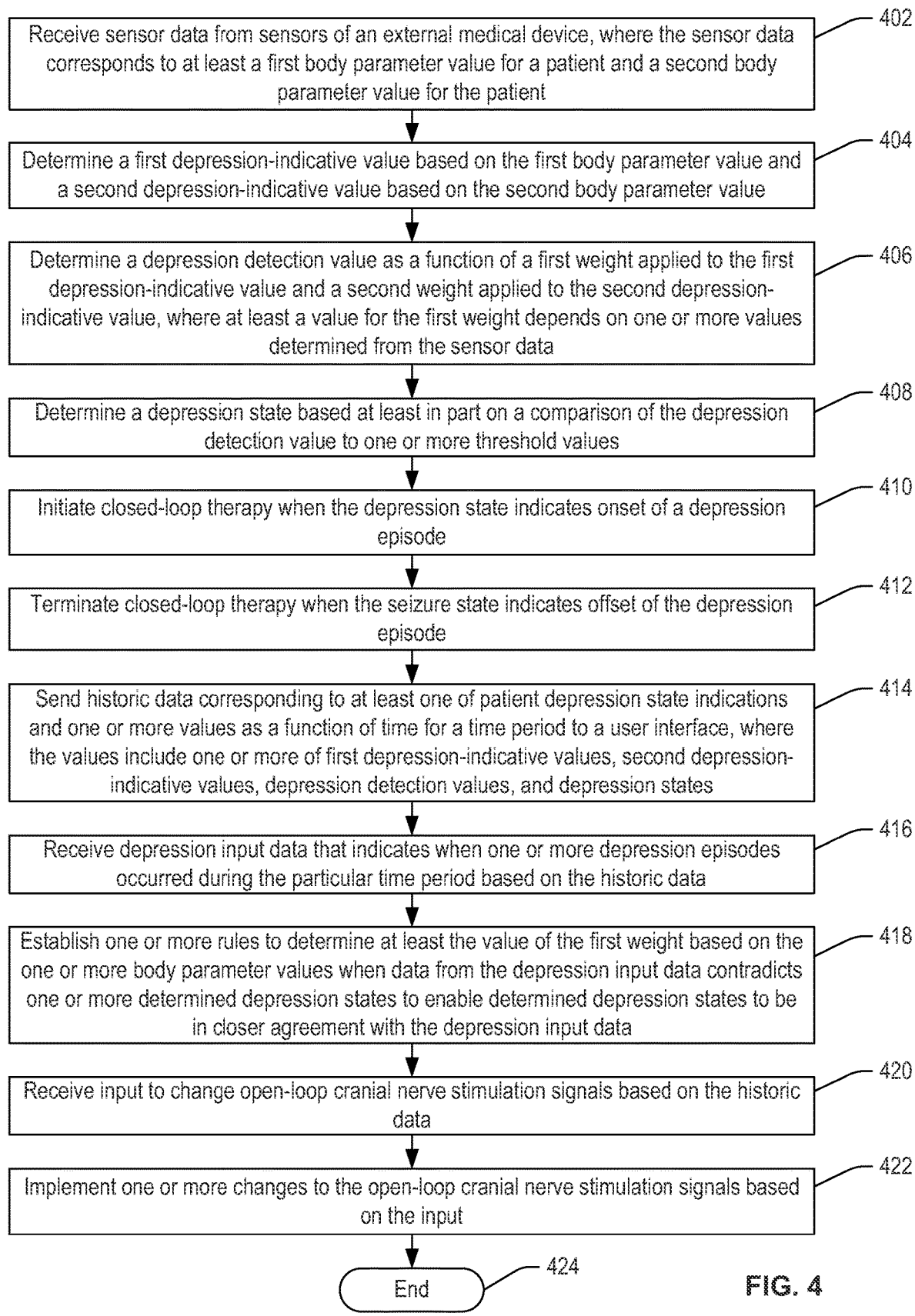
FIG. 4 is a flow chart of a second particular embodiment of a method of use of sensor data from a medical device that enables application of CNS signals to treat a depression disorder.

FIG. 4 is a flow chart of a second particular embodiment of a method of using CNS to treat a patient diagnosed with a depression disorder (e.g., major depressive disorder, dysthymia, seasonal affective disorder, and postpartum depression). The CNS may be applied by an external medical device coupled to a patient (e.g., the medical device system 100 depicted in FIG. 1). In an embodiment, the method may be performed by a processor. The processor may be the processor of the external medical device or the processor of a device that receives sensor data from the external medical device (e.g., the processor of a computer system associated with a healthcare provider). At 402, sensor data from sensors of an external medical device is received. The sensor data corresponds to at least a first body parameter value for the patient and a second body parameter value for the patient. The sensor data may be received as sensor data sets. Each sensor data set may correspond to a particular time and may include data associated with sensors of the external medical device. The sensors may include a temperature sensor, a conductivity sensor, an oximeter, a three axis accelerometer, a respiration sensor, a blood pressure sensor, a pedometer, other sensors, or combinations thereof.

The sensor data may include body parameter values or may enable the processor to calculate body parameter values corresponding to particular sensor data. For each sensor data set, the processor may store a time associated with the sensor data, the sensor data, values calculated based on the sensor data, or combinations thereof, as historic data. The values may include body parameter values, moving averages of body parameter values, change rates of body parameter values based on one or more previous sensor data sets, depression-indicative values, depression detection values, values associated with a depression state, or any combination thereof.

A first depression-indicative value based on the first body parameter value and a second depression-indicative value based on the second body parameter value may be determined, at 404. For example, the first depression-indicative value and the second depression-indicative value may be determined via application of Eqn 1 and Eqn 6.

A depression detection value may be determined by the processor, at 406. For example, the depression detection value may be determined as a function of a first weight applied to the first depression-indicative value and a second weight applied to the second depression-indicative value. The processor may determine the depression detection value by application of Eqn 7 and Eqn 8. At least a value for the first weight may depend on one or more values determined from the sensor data. For example, when the patient is exercising, sensor data may indicate that the heart rate of the patient is at a rate of over one hundred beats per minute for a relatively long period of time (e.g., for over 5 minutes or more), sensor data for skin temperature may be higher than a normal value, and sensor data for skin conductance may be a relatively large value. When the heart rate value is sustained over 100 beats per minute for the relatively long period of time, values of weights corresponding to the heart rate, the skin temperature, the respiration rate, and the skin conductance may be reduced and values of other weight factors (e.g., the weight corresponding to the blood oxygen saturation, the weight corresponding to the pedometer reading, the weight corresponding to the acceleration, or combinations thereof) may be increased. The values determined for the weights may be based on sets of rules that define a patient state. Rules may be set to accommodate various normal activities and lack of activity for the patient (e.g., rules to accommodate exercising, walking, and resting) and for the time of day. For example, a patient state may be defined by a set of rules for a sleep state, which may include rules associated with time of day, heart rate data, and accelerometer data. A patient state may also be defined for being awake, resting, exercising, or various other states. The values of the weights may be adjusted when the rules are met to enter and exit these patient states. Since different parameters may be more or less indicative of depression in each of these patient states, the weights associated with the different body parameters may be adjusted to more accurately detect a depression state. Time of day may also be used to adapt the weights to the patient's natural circadian rhythms, especially if the patient is more likely to experience depression at certain times of the day (e.g., night, morning, mid-day, evening). The weights may also be adjusted based on the time of year and/or the ambient temperature. For example, depression may be more common in the winter when the day light hours are fewer and the temperature is lower. The weights may also be adjusted based on a medication schedule and the type of medications being taken. For example, certain body parameter values may be less likely to indicate a depression state shortly after a certain medication is taken, but hours later the medication may have less of an effect on the body parameter.

A depression state may be determined based at least in part on a comparison of the depression detection value to one or more threshold values, at 408. The one or more threshold values may include a depression onset threshold, a depression offset threshold, or both. In some embodiments, the depression onset threshold is the same as the depression offset threshold. The depression state may be indicated by a depression onset value, a depression offset value, or both. The depression onset value and the depression offset value of the depression state may be determined using Eqn 11.

Closed-loop therapy may be initiated when the depression state indicates onset of a depression episode, at 410. The closed-loop therapy may include CNS signals, activation of a medicine delivery system, other treatment option, or combinations thereof. Closed-loop therapy may be terminated when the depression state indicates offset of the depression, at 412.

Historic data may be sent to an interface, at 414. The historic data may correspond to patient depression state indications, other values, or a combination thereof. The other values may include the first depression-indicative values, the second depression-indicative values, the depression detection values, the depression states, or a combination thereof. The patient depression state indications correspond to patient input that indicates when the patient experienced onset of a depression episode, offset of a depression episode, or both. The patient depression state indications may include patient input that confirms or contradicts determined depression states. The patient input may be received in response to a query from the external medical device. The interface may include a user interface that enables user input related to the historic data.

The historic data may be analyzed by the patient, by personnel associated with a healthcare provider, by one or more computers systems, or combinations thereof. Depression input data that indicates when one or more depression episodes occurred during the particular time period based on the historic data may be received, at 416. One or more rules to determine at least the value of the first weight based on the one or more body parameter values may be established when data from the depression input data contradicts one or more determined depression states to enable determined depression states to be in closer agreement with the depression input data, at 418. Establishing the one or more rules may include generating new rules, adjusting existing rules, or both. Statistical analysis, determining depression states using various weight values, other techniques, or combinations thereof may be used to establish the one or more rules.

For example, depression-indicative-values for four body parameter values may be determined from sensor data. A first rule may establish that each weight used in calculating the depression detection value based on depression-indicative values is 0.25 when the heart rate of the patient is in a normal range for the patient (e.g., from 50 beats per minute (bpm) to 65 bpm). Historic data for a month may indicate that depression state determinations using values of 0.25 for each weight agree with the depression input data about 60% of the time when the heart rate for the patient was in the normal range. Manipulation of the weights to alternate values (e.g., 0.55 for a first weight, 0 for a second weight, 0.40 for a third weight, and 0.05 for a fourth weight) may enable determined depression states using data that corresponds to when the heart rate of the patient was in the normal range during the particular time period to completely agree with the depression input data for corresponding times. In this example, the first rule may be adjusted so that the weight values are the alternate values that result in agreement with the depression input data.

In addition to enabling the change or addition of rules, the historic data may be used to change other values used during determination of depression states. For example, examination of the historic data may indicate to a healthcare provider that the one or more threshold values used to calculate the depression state should be adjusted. In this example, the healthcare provider may enter data that changes the one or more threshold values.

Input to change scheduled CNS signals based on the historic data may be received, at 420. For example, the input may be received from healthcare personnel. The input may change one or more parameters that define the scheduled CNS signals. For example, a healthcare provider may determine that depression onset occurs too frequently for the patient. In response to the determination, the healthcare provider may provide input to change one or more scheduled CNS signal parameters to shorten the time period between the scheduled CNS signals (e.g., from once per hour during waking hours to once per 45 minutes during waking hours). One or more changes may be implemented to the scheduled CNS signals based on the input, at 422. For example, the input may be sent to the external medical device and appropriate parameters of the scheduled CNS signals may be changed to new values to enable the external medical device to provide the scheduled CNS signals with the shortened time period between scheduled CNS signals as requested by the healthcare provider. The method may end, at 424.

Various embodiments disclosed herein enable a medical device system that is located substantially external to a patient to provide open-loop therapy and closed-loop therapy to the patient. One or more components of the medical device system (e.g., a vagus nerve stimulation system, one or more subcutaneous electrodes, at least a portion of a medicine delivery system, or combinations thereof) may be implanted in the patient. The medical device system enables application of open-loop therapy for the patient and closed-loop therapy for the patient. Open-loop therapy may be applied to the patient at intervals to inhibit depression episode occurrence, to reduce intensity of depression episodes that occur, to reduce duration of depression episodes that occur, or combinations thereof. Closed-loop therapy may be applied to the patient upon a determination of depression onset. Closed-loop therapy may be stopped upon a determination of depression offset. The closed-loop therapy may stop a depression episode, limit depression episode intensity, limit depression episode duration, or combinations thereof. Depression onset may be determined based on collected sensor data from the medical device system.

The medical device system may use historical data collected by the medical device system and depression indication data to customize the medical device system for the patient by adjusting values used to determine depression states (e.g., weight factors), by adjusting or creating rules used to determine depression states, by adjusting thresholds used to determine depression states, or combinations thereof. The depression indication data may be provided by the patient, by healthcare provider personnel, or both, based on analysis of the historical data. Customizing the medical device system for the patient may inhibit applications of closed-loop therapy when the patient is not experiencing depression onset.

The disclosure is described above with reference to drawings. These drawings illustrate certain details of specific embodiments of the systems and methods and programs of the present disclosure. However, describing the disclosure with drawings should not be construed as imposing on the disclosure any limitations that may be present in the drawings. The present disclosure contemplates methods, systems, and instructions on non-transitory computer-readable media that are executable by a processor for accomplishing particular tasks. The processor may be a general computer processor, a special purpose computer processor, or a hard-wired system.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive. Although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments.

The Abstract of the Disclosure is provided with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above-disclosed subject matter is to be considered illustrative, and not restrictive, and the appended claims are intended to cover all such modifications, enhancements, and other embodiments, which fall within the scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method comprising:
receiving sensor data at a processor from one or more sensors of a medical device, wherein the sensor data corresponds to at least a first body parameter value for a patient and a second body parameter value for the patient;
determining, via the processor, a first depression-indicative value based on the first body parameter value and a second depression-indicative value based on the second body parameter value;
determining, via the processor, a first weight and a second weight;
determining, via the processor, a depression detection value as a function of, in part, the first weight applied to the first depression-indicative value and the second weight applied to the second depression-indicative value;
determining, via the processor, a depression state based at least in part on a comparison of the depression detection value to a first threshold value and a second threshold value different from the first threshold value, the first threshold value associated with an onset of a depression episode, the second threshold value associated with an offset of the depression episode; and
in response to determining that the depression state indicates depression onset, initiating, via the processor, neurostimulation therapy by one or more electrodes.

2. The method of claim 1, further comprising automatically adjusting, via the processor, at least one of the first weight or the second weight in response to an indication contradicting the depression state.

3. The method of claim 2, wherein the indication is included in depression data, the depression data comprising at least one of patient input data, historic data corresponding to values as a function of time, or second sensor data from one or more sensors.

4. The method of claim 1, wherein the neurostimulation therapy initiated in response to determining that the depression state indicates depression onset is a closed-loop therapy.

5. The method of claim 4, wherein the closed-loop therapy comprises cranial nerve stimulation (CNS), and wherein the CNS comprises external trigeminal nerve stimulation (TNS), vagus nerve stimulation (VNS), or a combination thereof.

6. The method of claim 1, further comprising adjusting, via the processor, the first weight based on a state of current physical activity of the patient relating to a current level of exercise of the patient.

7. The method of claim 6, wherein the state of activity comprises one or more of an awake state, a resting state, a sleeping state, or an exercise state.

8. The method of claim 1, further comprising setting, via the processor, an initial value of the first weight and an initial value of the second weight based on an input from a health care provider, based on the sensor data, based on historic data, or based on a selected patient population.

9. The method of claim 1, wherein determining the first depression-indicative value comprises calculating, via the processor, the first depression-indicative value as a ratio of a first moving average value of the first body parameter value over a first time period to a second moving average value of the first body parameter value over a second time period.

10. The method of claim 1, wherein the first body parameter value is a skin temperature, skin conductance, heart rate, change in heart rate, blood oxygen saturation, acceleration, respiration rate, or a value determined as a combination thereof.

11. The method of claim 1, further comprising:
comparing, via the processor, a trend of one or more body parameter values as a function of time to at least one trend threshold; and
outputting, via the processor, a recommendation when the trend satisfies at least one trend threshold, wherein the recommendation is associated with a prompt to take one or more actions to inhibit a depression episode in the patient.

12. A system comprising:
a processing unit comprising a processor and a memory storing instructions that are executable by the processor to:
receive first sensor data corresponding to a first body parameter value for a patient from a first sensor;
receive second sensor data corresponding to a second body parameter value for the patient from a second sensor;
determine a first depression-indicative value based on the first body parameter value and determine a second depression-indicative value based on the second body parameter value;
determine a first weight and a second weight;
determine a depression detection value as a function of, in part, the first weight applied to the first depression-indicative value and the second weight applied to the second depression-indicative value;
determine a depression state based at least in part on a comparison of the depression detection value to a first threshold value and a second threshold value different from the first threshold value, the first threshold value associated with an onset of a depression episode, the second threshold value associated with an offset of the depression episode; and
in response to determining that the depression state indicates depression onset, initiate neurostimulation therapy by one or more electrodes.

13. The system of claim 12, wherein the instructions are further executable by the processor to adjust at least one of the first weight or the second weight in response to an indication contradicting the depression state.

14. The system of claim 12, wherein the neurostimulation therapy initiated in response to determining that the depression state indicates depression onset is a closed-loop therapy.

15. The system of claim 12, wherein the instructions are further executable by the processor to adjust the first weight based on a state of current physical activity of the patient relating to a current level of exercise of the patient.

16. The system of claim 15, wherein the state of activity includes one or more of an awake state, a resting state, a sleeping state, or an exercise state.

17. The system of claim 12, wherein the first body parameter value is skin temperature, skin conductance, heart rate, change in heart rate, blood oxygen saturation, acceleration, respiration rate, or a value determined as a combination thereof.

18. A non-transitory computer-readable medium comprising instructions executable by a processor to:
determine a first depression-indicative value based on a first body parameter value for a patient and a second depression-indicative value based on a second body parameter value for the patient;
determine a first weight and a second weight;
determine a depression detection value based in part on the first weight and the first depression-indicative value and based in part on the second weight and the second weight and the second depression-indicative value;
determine a depression state based at least in part on a comparison of the depression detection value to a first threshold value and a second threshold value different from the first threshold value, the first threshold value associated with an onset of a depression episode, the second threshold value associated with an offset of the depression episode; and
in response to determining that the depression state indicates depression onset, initiate neurostimulation therapy by one or more electrodes.

19. The non-transitory computer-readable medium of claim 18, further comprising instructions executable by the processor to perform at least one of:
adjusting the first weight based on a current state of physical activity of the patient relating to a current level of exercise of the patient; or
adjusting at least one of a first set of rules used to determine the first weight or a second set of rules used to determine the second weight based on sensor data for the patient that indicates depression onsets and offsets.

20. The non-transitory computer-readable medium of claim 18, wherein the neurostimulation therapy initiated in response to determining that the depression state indicates depression onset is a closed-loop therapy.

* * * * *